(12) United States Patent
Ruemer et al.

(10) Patent No.: US 8,620,596 B2
(45) Date of Patent: *Dec. 31, 2013

(54) SYSTEM AND METHOD FOR SORTING DATA

(75) Inventors: Robert Ruemer, Nanuet, NY (US);
Narayan Ragunathan, West Nyack, NY (US); Robert A. Femia, Kinnelon, NJ (US)

(73) Assignee: Par Pharmaceutical, Inc., Woodcliff, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/185,599

(22) Filed: Jul. 19, 2011

(65) Prior Publication Data

US 2012/0046879 A1  Feb. 23, 2012

Related U.S. Application Data

(63) Continuation of application No. 12/466,135, filed on May 14, 2009, now Pat. No. 7,996,170, which is a continuation of application No. 11/810,651, filed on Jun. 6, 2007, now Pat. No. 7,552,020, which is a continuation of application No. 11/150,614, filed on Jun. 10, 2005, now Pat. No. 7,246,020.

(51) Int. Cl.
*G01N 31/00* (2006.01)

(52) U.S. Cl.
USPC ............................................. 702/27; 702/189

(58) Field of Classification Search
USPC .............................................. 702/83, 27, 189
See application file for complete search history.

(56) References Cited

U.S. PATENT DOCUMENTS

| | | | | | |
|---|---|---|---|---|---|
| 3,863,489 | A | * | 2/1975 | Ayers et al. | 73/23.36 |
| 5,398,539 | A | * | 3/1995 | Gordon et al. | 73/23.35 |
| 5,960,435 | A | * | 9/1999 | Rathmann et al. | 1/1 |
| 6,329,652 | B1 | * | 12/2001 | Windig et al. | 250/282 |
| 6,493,639 | B1 | * | 12/2002 | Quimby et al. | 702/22 |
| 6,959,252 | B2 | * | 10/2005 | Tai et al. | 702/84 |
| 7,246,020 | B2 | * | 7/2007 | Ruemer et al. | 702/83 |
| 7,552,020 | B2 | * | 6/2009 | Ruemer et al. | 702/83 |
| 7,996,170 | B2 | * | 8/2011 | Ruemer et al. | 702/83 |
| 8,010,223 | B2 | * | 8/2011 | Yamaguchi et al. | 700/170 |
| 2003/0036856 | A1 | * | 2/2003 | Excoffier | 702/19 |
| 2003/0235858 | A1 | * | 12/2003 | Gopalan et al. | 435/7.1 |
| 2004/0110193 | A1 | * | 6/2004 | Castle et al. | 435/6 |
| 2006/0104518 | A1 | * | 5/2006 | Yang et al. | 382/224 |

* cited by examiner

*Primary Examiner* — Michael Nghiem
(74) *Attorney, Agent, or Firm* — Arent Fox LLP

(57) ABSTRACT

A method and apparatus that enables a user to sort data from one or more sample lots, which may be obtained via a network, such as the Internet, into a composite parameter structure. The composite parameter structure is a function of one or more parameters corresponding to one or more characteristics associated with one or more sample lots. The composite parameter structure representation may be printed, stored, or transmitted to another location. A server device that is coupled and working in conjunction with a client device may implement the present invention.

15 Claims, 14 Drawing Sheets

1000

| m/z | Characteristic # | Lot A (RRT) | Lot B (RRT) | Lower Boundary (RRT) | Upper Boundary (RRT) |
|---|---|---|---|---|---|
| 365 | 1 | 0.07840 | 0.07124 | 0.00000000 | 0.26982028 |
| 365 | 2 | | 0.46848 | 0.26989972 | 0.47306908 |
| 365 | 3 | | 0.47766 | 0.47307092 | 0.48471359 |
| 365 | 4 | 0.49327 | 0.49177 | 0.48471641 | 0.51209094 |
| 365 | 5 | | 0.53242 | 0.51209907 | 0.54657717 |
| 365 | 6 | | 0.56074 | 0.54658283 | 0.57630189 |
| 365 | 7 | | 0.59187 | 0.57630811 | 0.61782981 |
| 365 | 8 | | 0.64380 | 0.61784019 | 0.64661444 |
| 365 | 9 | 0.64805 | 0.64943 | 0.64661556 | 0.65248439 |
| 365 | 10 | 0.65579 | 0.65554 | 0.65248561 | 0.65945422 |
| 365 | 11 | | 0.66337 | 0.65945578 | 0.67278812 |
| 365 | 12 | | 0.68221 | 0.67279188 | 0.68512942 |
| 365 | 13 | 0.68607 | 0.68805 | 0.68513058 | 0.69104440 |
| 365 | 14 | | 0.69404 | 0.69104560 | 0.69761429 |
| 365 | 15 | | 0.70119 | 0.69761572 | 0.71158292 |
| 365 | 16 | | 0.72198 | 0.71158708 | 0.72769886 |
| 365 | 17 | 0.72981 | 0.73342 | 0.72770114 | 0.74660736 |
| 365 | 18 | | 0.75980 | 0.74661264 | 0.77529690 |
| 365 | 19 | | 0.79080 | 0.77530310 | 0.80776161 |
| 365 | 20 | | 0.82473 | 0.80776839 | 0.83996195 |
| 365 | 21 | | 0.85520 | 0.83996805 | 0.87101684 |
| 365 | 22 | 0.88863 | 0.88684 | 0.87102316 | 0.88992938 |
| 365 | 23 | | 0.89302 | 0.88993062 | 0.90170326 |
| 365 | 24 | | 0.91039 | 0.90170674 | 0.93067594 |
| 365 | 25 | | 0.95097 | 0.93068406 | 0.96423735 |
| 365 | 26 | | 0.97751 | 0.96424265 | 0.98639822 |
| 365 | 27 | 0.99529 | 0.99529 | 0.98640178 | 0.99934919 |
| 365 | 28 | 1.00471 | 1.00341 | 0.99935081 | 1.01464775 |
| 365 | 29 | | 1.02589 | 1.01465225 | 1.03525813 |
| 365 | 30 | | 1.04463 | 1.03526187 | 1.06285635 |
| 365 | 31 | 1.06494 | 1.08109 | 1.06286365 | 1.11275867 |
| 365 | 32 | | 1.14444 | 1.11277134 | 1.23976593 |
| 365 | 33 | 1.33513 | 1.33513 | 1.23980407 | 50.00000000 |

FIG.10

SYSTEM AND METHOD FOR SORTING DATA

CROSS-REFERENCE TO RELATED APPLICATIONS

This application is a continuation of U.S. patent application Ser. No. 12/466,135 filed May 14, 2009, now U.S. Pat. No. 7,996,170, which is a continuation of U.S. patent application Ser. No. 11/810,651, filed Jun. 6, 2007, now U.S. Pat. No. 7,552,020, which is a continuation of U.S. patent application Ser. No. 11/150,614, filed Jun. 10, 2005, now U.S. Pat. No. 7,246,020, each of which is hereby incorporated by reference herein in its entirety.

BACKGROUND

1. Field of the Invention

This invention relates generally to a system and method for sorting data. More particularly, the present invention relates to a system for sorting data sample lots into a composite parameter structure without the use of a reference standard.

2. Background Discussion

Conventional data sorting techniques for sample lots typically use a reference standard to identify specific data or aggregate data using a group-by field process. Data manipulation techniques that do not rely on reference standards generally seek to resolve or separate sample data for further analysis. One definition of a reference standard is a substance that has been shown by an extensive set of analytical tests, to be authentic material of high purity. This standard may be obtained from a recognized source or may be prepared by independent synthesis or by further purification of existing production material. Another definition of a reference standard is a substance of established quality and purity, as shown by comparison to a primary reference standard, used as a reference standard for routine laboratory analysis.

Yet another definition of a reference standard is a drug, chemical, or dosage form of specified properties used as the basis for quantitative comparison with other materials of qualitatively similar properties. The purpose of such a comparison is to express the amount or degree of the designated property in the "other" material as a fraction or multiple of the amount or degree of the property contained in the standard. The reference standard serves as a unit of measurement for the properties of the other, or "unknown," material. Even physical systems of measurement are based on reference standards. The use of reference standards is of particularly great importance to the design and interpretation of biological experiments. In biological experiments, particularly, variability and instability of the biological test system can markedly influence the apparent effects and effectiveness of substances being tested.

One example of a conventional sorting technique is described in U.S. Pat. No. 5,960,435, issued to Rathman, entitled, "Method, System, and Computer Program for Computing Histogram Aggregations." This patent relates to a data record transformation that computes histograms and aggregations for an incoming record stream. The data record transformation computes histograms and aggregations and operates in a streaming fashion on each record in an incoming record stream. A limited number of records are operated on during a particular time, thereby minimizing the memory requirements. A data transformation unit includes a binning module and a histogram aggregation module. The histogram aggregation module processes each binned and sorted record to form an aggregate record in a histogram format. Data received in each incoming binned and sorted record is expanded and accumulated in an aggregate record for matching group-by fields. An associative data structure holds a collection of partially aggregated histogram records. A histogram aggregation module processes each binned record to form an aggregate record in a histogram format. Input records from the unordered record stream are matched against the collection of partially aggregated histogram records and expanded and accumulated into the aggregate histogram record having matching group-by fields. This patent is hereby incorporated by reference in its entirety herein.

Another example of a conventional sorting technique is described by U.S. Patent Application Publication No. 2003/0036856, applied by Excoffier, entitled, "Method and System for Classifying Chromatograms." This application relates to a method and system for chromatogram analysis in which a chromatogram is reduced to a data set that can be compared to another such data set, producing a comparison result that indicates the similarity or dissimilarity of the two chromatograms. This can be used to identify DNA sequence variations through chromatogram analysis. This patent application is hereby incorporated by reference in its entirety herein.

Furthermore, U.S. Pat. No. 5,398,539, issued to Gordon, entitled, "Correlated Multi-Dimensional Chromatography with Confirmatory Hybrid Run" relates to a correlated two-dimensional gas chromatography system, in which peaks from one chromatogram are associated, or "paired" with respective peaks of another chromatogram. Both peaks of a pair should correspond to the same sample component. A hybrid chromatographic column is designed so that the retention time of a sample component is the average of the retention times of that component in the two independent columns. Thus, a peak location in the hybrid chromatogram can be calculated for each pair of peaks. The absence of a peak at that location or the inconsistency of the area of a peak at that location disconfirms the pairing. The invention also provides for higher dimensional systems and for other separation technologies. This patent is hereby incorporated by reference in its entirety herein.

While the above-described patents and patent application provide techniques to sort and classify data samples, none of these conventional approaches provide a method to sort data in a sample lot without a reference standard to identify specific data components or a group-by field to aggregate data. Unfortunately, conventional techniques that do not rely on reference standards are also not adequate, because these techniques only serve to resolve the peaks and do not compare the peaks between sample lots. Thus, it would be an advancement in the state of the art to sort data into a composite parameter structure without a reference standard.

BRIEF SUMMARY OF THE INVENTION

The present invention is directed toward a method and apparatus that enables sorting data, such as chromatographic data, from sample lots. A composite parameter structure (such as a bin structure) is generated based on characteristics associated with each sample lot and may be dynamically adjusted based on the data in each sample lot. These characteristics may be, for example, relative retention time or a peak. The composite parameter structure representation may be printed, stored or transmitted to another location.

Accordingly, one embodiment of the present invention relates to a method and apparatus for establishing a composite parameter structure, which may be a dynamic iterative structure, from sample lots. Characteristics associated with a first sample lot are first identified. For each characteristic of the first sample lot, parameters corresponding to the characteristics of the first sample lot are identified. Characteristics associated with a second sample lot are then identified. The characteristics associated with the second sample lot are compared to the parameters corresponding to the characteristics of the first sample lot. For each characteristic of the second sample lot that does not correspond to the parameters corresponding to the characteristic of the first sample lot, additional parameters are established.

Another embodiment of the present invention relates to the embodiment described above and, further, establishing a composite parameter structure as a function of the parameters corresponding to the characteristics of the first sample lot and the additional parameters corresponding to the characteristics of subsequent sample lots.

Yet another embodiment of the present invention relates to the embodiment described above and, further, modifying the boundaries of the composite parameter structure as a function of the characteristics associated with the first sample lot and the subsequent sample lots.

Yet another embodiment of the present invention relates to a method and apparatus for establishing a composite parameter structure as a function of parameters associated with the characteristics of the first sample lot and the parameters associated with the characteristics of additional sample lots. Characteristics associated with a first sample lot are identified. For each of the characteristics of the first sample lot, parameters corresponding to each of the characteristics of the first sample lot are identified. Characteristics associated with a second sample lot are identified. For each of the characteristics of the second sample lot, parameters corresponding to each of the characteristics of the first sample lot are identified. The parameters associated with the characteristics of the second sample lot are compared to the parameters associated with the characteristics of the first sample lot. A composite parameter structure is established as a function of the parameters associated with the characteristics of the first sample lot and the parameters associated with the characteristics of the second sample lot.

Yet another embodiment of the present invention relates to the method described above and, further, establishing a composite parameter structure as a function of the parameters associated with the characteristics of the first sample lot, the parameters associated with the characteristics of the second sample lot, and the parameters associated with the characteristics of the subsequent sample lots.

Yet another embodiment of the present invention relates to the method described above and, further, modifying the boundaries of the composite parameter structure as a function of the characteristics of the first sample lot and the subsequent sample lots.

BRIEF DESCRIPTION OF THE DRAWINGS

FIG. 10 shows a table generated by the invention.

DETAILED DESCRIPTION OF THE INVENTION

Figure 1:
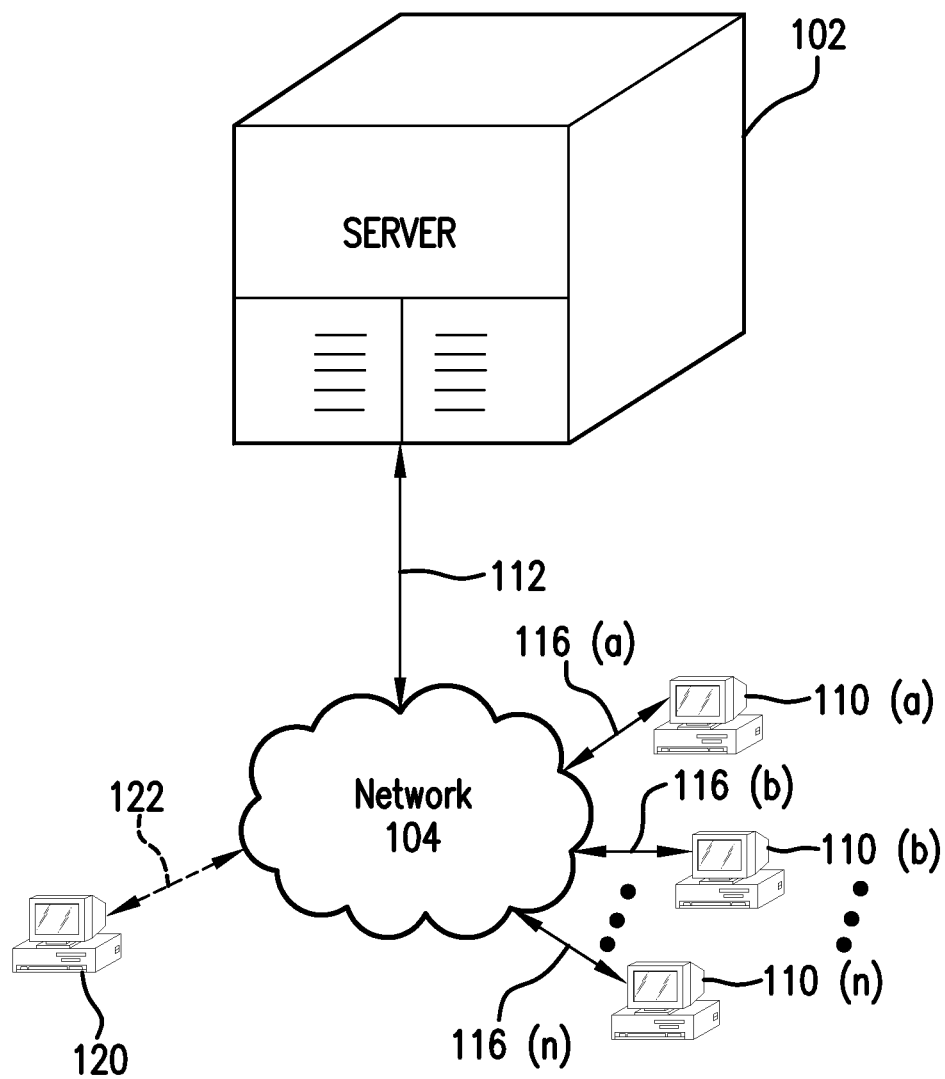
FIG. 1 shows a network environment adapted to support the present invention.

Generally, this invention relates to a system and method for sorting data. More particularly, this invention relates to a system for sorting data from sample lots using a composite parameter structure.

While it is possible to apply this invention to a variety of data, one embodiment of the present invention may be used to provide a method for matching peaks or other characteristics from multiple lots of data generated, for example, by a two-dimensional separation technique, or other separation methods without the use of a reference standard or a group-by field.

The present invention provides a data sorting solution for complex compositions, such as biologically derived products, where it may be impractical or impossible to use a reference standard or group-by field to identify specific data components or aggregate data. Because of the unique and often complex nature of biological products, conventional data sorting techniques have not provided a reliable method for determining bioequivalence between reference listed drugs or biological licensed products and generic formulations, which are regulated for marketing by the U.S. Food and Drug Administration (FDA).

An embodiment of this invention is formulating a generic version of the reference listed drug Premarin® (conjugated estrogens), which is manufactured from pregnant mares' urine. Pregnant mares' urine contains a variety of steroids. Both the concentration and type of steroid, produced in the urine, can vary from one sample lot to another sample lot. The data produced from the separation of the various lots of urine, therefore, will also vary. The FDA has stated that while Premarin® is not adequately characterized, the agency could approve a generic version that originates from a natural source material (pregnant mares' urine) before all of the active ingredients are defined, provided that a detailed chemical composition of the product was known. This invention solves the problem, therefore, of statistically matching like or similar peaks, which represent steroids, and separating out unlike unique or distinct peaks by use of a software solution, in a processing system further described, which would be useful to characterize such complex materials and could potentially be used to demonstrate bioequivalence between a reference listed drug, such as Premarin®, and a generic formulation.

Data may be produced for a formulation, compound, or a drug, such as Premarin®, by first using a separation technique that separates the compound by atomic mass and then by a column chromatography technique. The resultant two-dimensional data may then be provided in atomic mass units (m/z) and retention time (RT). A quantitative standard is used in the second dimension to create a relative retention time (RRT), however this does not identify specific data components or aggregate data. Instead, the RRT enables the matching of RT from sample lot to sample lot. The data is then grouped by atomic mass units. Within each m/z group, the RRTs are distributed into parameters. One set of parameters corresponds to each RRT or peak. Additional sample lots of data may be then matched with the parameter structure developed for the first lot. However, if more than one peak from the second lot exists in any single parameter, new parameters will be created to sort the additional peaks. Whenever the parameter structure is changed, all the existing lots are re-fit into the new parameter structure. This is referred to as a composite parameter structure herein, which may involve the modification of the parameters.

In one embodiment of the invention, the composite parameter structure is produced using an iterative process, which is complete when each parameter contains only one peak per lot of data. The result of this process creates a composite parameter structure that sorts like peaks, corresponding to like compounds, effectively characterizing complex materials such as the biologically-derived product, Premarin®. Once a sufficient quantity of lots has been processed in this manner, subsequent lots may be compared to the composite parameter structure to determine bioequivalence, quality control, or for other subsequent analysis. This sorting technique, therefore, addresses the problem of determining bioequivalence for previously inadequately characterized, complex biological materials, currently evading FDA approval of generic versions.

One example of the present invention is characterizing, or identifying, three lots of data that originate from a single source. Each lot typically varies somewhat by some arbitrary unit of measurement (aum). Some lots typically have more or less data points. The goal is to match the like points and identify the unique points. For example, lot A has the following three data points: Point 1A=1.0 aum, Point 2A=2.0 aum, and Point 3A=3.0 aum. The invention solves the problem and sorts the data in the following manner: each data point is placed in the center of a parameter, or bin, with a defined lower boundary and a defined upper boundary. The width of the parameter in aum is determined by taking all the points in the sample lot and finding a midpoint between each. Each, mid or, middle point then becomes a parameter boundary. However, the parameter boundaries do not overlap and peaks are not located at the parameter boundary. The parameter boundary width or "wall" is a mathematical quantity derived as a function of an algorithm. The definition typically results in a parameter boundary quantity represented by more significant figures than the sample lot data. The lower parameter boundary and upper parameter boundary are predefined based on the universe of data (components) in the analyzed data. The lower and upper parameter wall boundaries are also described herein as the "limit".

In another embodiment of the invention, parameters corresponding to a particular characteristic, such as a relative retention time (RRT) or peak, are first established for each sample lot. After all of the parameters have been established, a composite parameter structure is established by comparing the parameters of each sample lot, adding new parameters and adjusting the boundaries of the composite parameter structure as needed to ensure that each characteristic, such as a RRT or peak for any single lot, is contained in a separate parameter or bin. The result of this process also creates a composite parameter structure that sorts like peaks, corresponding to like compounds, effectively characterizing complex materials. For example, the biologically-derived product, Premarin®, can be characterized. Once sufficient sample lots have been processed in this manner, subsequent sample lots may be compared to the composite parameter structure to determine bioequivalence, quality control, or for other subsequent analysis. This sorting technique, therefore, also solves the problem of determining bioequivalence for inadequately characterized, complex biological materials, currently evading FDA approval of generic versions.

This invention may be implemented using one or more processing devices. The processing devices may be coupled such that portions of the processing and/or data manipulation may be performed at one or more processing devices and shared or transmitted between a plurality of processing devices. Thus, an example of the invention is described in a network environment. Specifically, FIG. 1 shows a network environment 100 adapted to support the present invention. The exemplary environment 100 includes a network 104, a server 102, a plurality of communication appliances, or user locations, or subscriber devices, or client terminals, 110(a) ... (n) (where "n" is any suitable number) (collectively referred to herein as, client terminals 110) and the remote client terminals, represented by terminal 120.

The network 104 is, for example, any combination of linked computers, or processing devices, adapted to transfer and process data. The network 104 may be private Internet Protocol (IP) networks, as well as public IP networks, such as the Internet that can utilize World Wide Web (www) browsing functionality.

Server 102 is operatively connected to network 104, via bi-directional communication channel, or interconnector, 112, which may be for example a serial bus such as IEEE 1394, or other wire or wireless transmission medium. The terms "operatively connected" and "operatively coupled", as used herein, mean that the elements so connected or coupled are adapted to transmit and/or receive data, or otherwise communicate. The transmission, reception or communication is between the particular elements, and may or may not include other intermediary elements. This connection/coupling may or may not involve additional transmission media, or components, and may be within a single module or device or between the remote modules or devices.

The server 102 is adapted to transmit data to, and receive data from, client terminals 110 and 120, via the network 104. Server 102 is described in more detail with reference to FIG. 2, herein.

Client terminals 110 and 120 are typically computers, or other processing devices such as a desktop computer, laptop computer, personal digital assistant (PDA), wireless handheld device, and the like. They may be capable of processing and storing data themselves or merely capable of accessing processed and stored data from another location (i.e., both thin and fat terminals). These client terminals 110, 120 are operatively connected to network 104, via bi-directional communication channels 116, 122, respectively, which may be for example a serial bus such as IEEE 1394, or other wire or wireless transmission medium. Client terminals 110, 120 are described in more detail in relation to FIG. 3.

The server 102 and client terminals 110, 120 typically utilize a network service provider, such as an Internet Service Provider (ISP) or Application Service Provider (ASP) (ISP and ASP are not shown) to access resources of the network 104.

Figure 2:
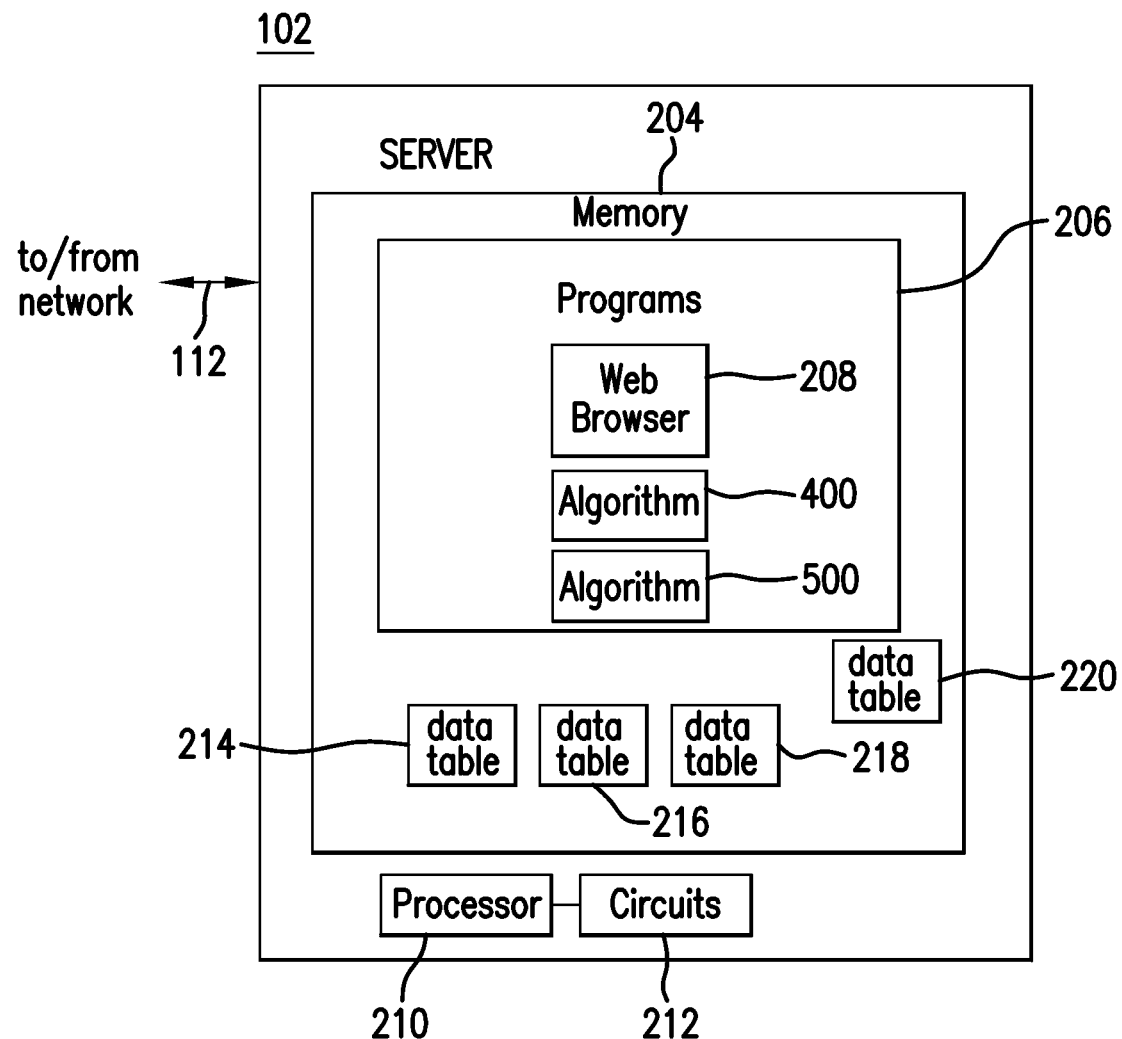
FIG. 2 illustrates a processing apparatus adapted to store and process data related to the present invention.

FIG. 2 illustrates that server 102, which is adapted to store and process data related to the present invention, is operatively connected to the network (shown as 104 in FIG. 1), via interconnector 112. Server 102 includes a memory 204, processor 210 and circuits 212.

Memory 204 stores programs 206, which include, for example, a web browser 208, algorithms 400 and 500, as well as typical operating system programs (not shown), input/output programs (not shown), and other programs that facilitate operation of server 102. Web browser 208 is for example an Internet browser program such as Internet Explorer™. Algorithms 400 and 500 are a series of steps for manipulating selected data, which is typically stored on a computer-readable memory and executed by a processor. The sorting process of the present invention typically generates a representation of the sample lot data and composite parameter structure. These functions may be implemented or facilitated by using software or other program code to sort the data and generate the representation. The algorithm 400 is discussed in more detail in relation to FIGS. 4 and 6 and algorithm 500 is discussed in more detail in relation to FIGS. 5 and 7.

Memory 204 also stores data tables 214, 216, 218, and 220. These data tables are databases or memory locations adapted to store related data, which can be retrieved, processed, updated, modified or otherwise manipulated.

For example, data table 214 may be adapted to store data related to a first sample lot; data table 216 may be adapted to store data related to a second sample lot; and data table 218 may be adapted to store data related to a third sample lot. Data table 220 may be adapted to store a composite parameter structure developed by the sorting process described in the invention. A sample lot could include, for example, a biological sample, such as pregnant mares' urine. This data is typically obtained following a separation technique, for example a separation technique that separates the sample first by atomic mass of the molecule (m/z) and then by retention time (RT) on or from a chromatographic column. To facilitate matching of lot-to-lot, an additional standard may be used in a second dimension to create, for example, a relative retention time (RRT) but may not identify specific data components or aggregate data. Alternatively, RT and then m/z, or any other orthogonal technique could first separate a sample lot. An orthogonal technique is an independent technique for analyzing the components separated in the sample lot e.g., mass spectrometry (MS), flame ionization detector (FID), or ultraviolet spectrometry (UV).

Data table 220 may be adapted to store the composite parameter structure, which includes the representation of sample data lots as a function of the characteristics of the first sample lot, the characteristics of the second sample lot, and the characteristics of a third sample lot, and any additional sample lots. The number of sample lots may include "n" sample lots, where "n" is any suitable number or quantity.

Processor 210, which is operatively connected to memory 204, is used to process and manipulate the data retrieved and stored by server 102 or from another device coupled to network 104. The processor 210 is typically a microprocessor with sufficient speed and processing capacity to adequately perform the desired data manipulations, of server 102. Circuits 212 are operatively connected to processor 210 and typically include, for example, Integrated Circuits (ICs), ASICs (application specific ICs) power supplies, clock circuits, cache memory and the like, as well as other circuit components that assist in executing the software routines stored in the memory 204 and that facilitate the operation of processor 210.

Figure 3:
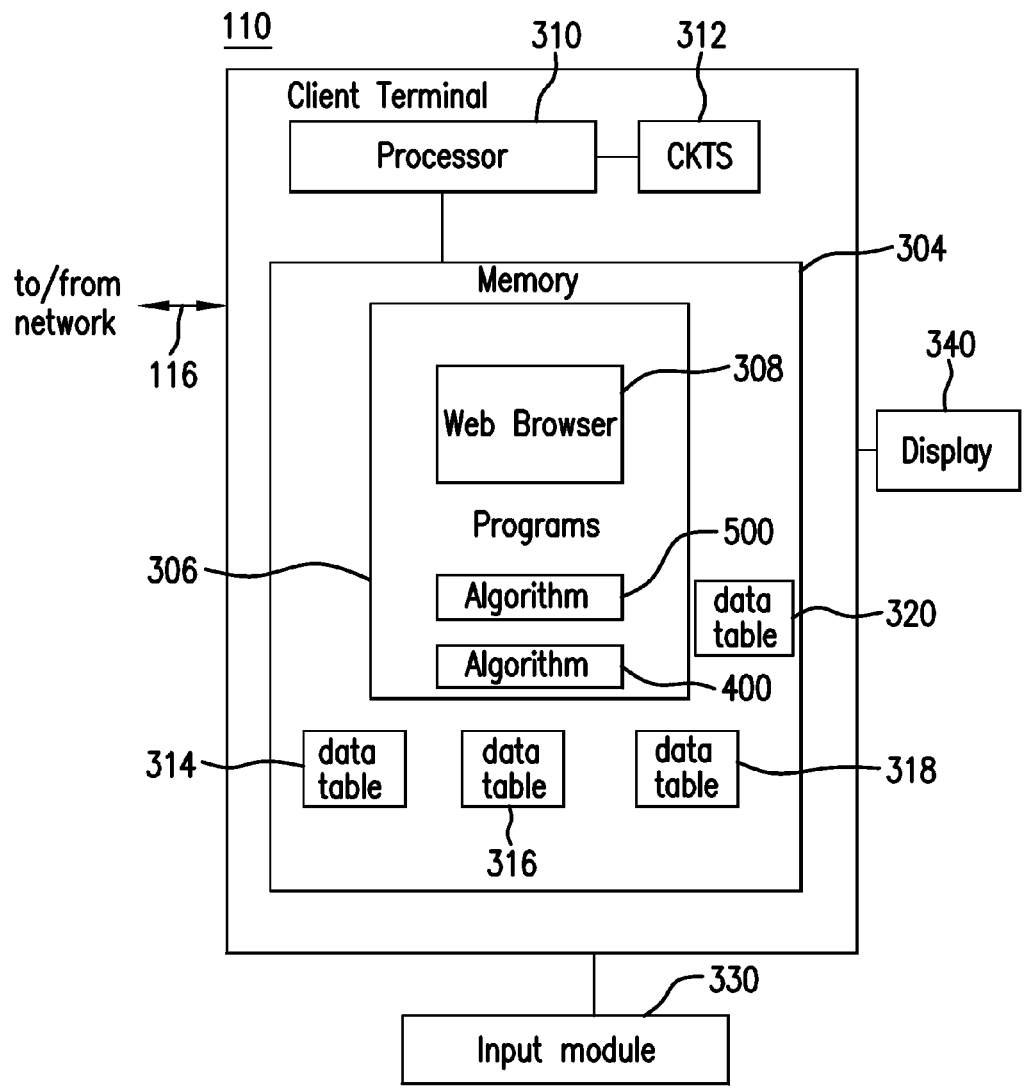
FIG. 3 illustrates a communication appliance shown in FIG. 1.

FIG. 3 illustrates subscriber terminal, also referred to herein as a client terminal, user terminal, or communication appliance 110. Terminal 110 is typically a desktop computer, laptop computer, PDA (personal digital assistant), wireless handheld device, mobile phone or other device capable of interfacing with a network, such as an IP network. Terminal 110 includes processor 310, support circuitry 312, memory 304, input module 330 and display module 340. Bi-directional interconnection medium 116 operatively connects the terminal 110 to the network (shown as element 104 in FIG. 1). The user terminal is typically located at the user location.

Processor 310, which is operatively connected to memory 304, is used to process and manipulate the data retrieved and stored by terminal 110. The processor 310 is typically a microprocessor with sufficient speed and processing capacity. The processor 310 is operatively connected to circuitry 312. Circuitry 312 typically includes, for example, Integrated Circuits (ICs), ASICs (application specific ICs) power supplies, clock circuits, cache memory and the like, as well as other circuit components that assist in executing the software routines stored in the memory 304 and that facilitate the operation of processor 310.

Memory 304 stores programs 306, which include, for example, a web browser 308, algorithms 400 and 500 as well as typical operating system programs (not shown), input/output programs (not shown), and other programs that facilitate operation of terminal 110. Web browser 308 is for example an Internet browser program such as Internet Explorer™. Algorithms 400 and 500 are a series of steps, typically executed by a processor such as, for example, processor 310, to manipulate selected data from the client terminal. Algorithm 400 is discussed in more detail in relation to FIGS. 4 and 6 and algorithm 500 is discussed in more detail in relation to FIGS. 5 and 7.

Memory 304 also stores data tables 314, 316, 318, and 320. These data tables are databases or memory locations adapted to store related data, which can be retrieved, processed, updated, modified or otherwise manipulated.

Data table 314 is adapted to store data related to a first sample lot; data table 316 is adapted to store data related to a second sample lot; and data table 318 is adapted to store data related to a third sample lot. Alternatively, another design approach would use relational database design where all the data points, from all the lots, are stored in one table and other tables store information about the data points. In this alternative approach, primary and foreign keys would then be used to join information across the tables. Data table 320 is adapted to store the composite parameter structure developed by the sorting process described in the invention. As described previously herein, a sample lot could include, for example, a biological sample, such as pregnant mares' urine. This data is typically obtained following a separation technique, for example a separation technique that separates the sample first by atomic mass of the molecule (m/z) and then by retention time (RT). To enable the matching of lot-to-lot, an additional standard may be used in a second dimension to create, for example, a relative retention time (RRT) but may not identify specific data components or aggregate data. Alternatively, RT and then m/z, or any other orthogonal technique could first separate a sample lot. An orthogonal technique is an independent technique for analyzing the components separated in the sample lot e.g., mass spectrometry (MS), flame ionization detector (FID), or ultraviolet spectrometry (UV).

Input module 330 is, for example, a keyboard, mouse, touch pad, menu having soft-keys, or any combination of such elements, or other input facility adapted to provide input to terminal 110.

Display module 340 is, for example, a monitor, LCD (liquid crystal display) display, GUI (graphical user interface) or other interface facility that is adapted to provide or display information to a user. Other display modules could include a printer or other output module.

Generally, the present invention is achieved in several steps. A general discussion of several embodiments of the invention are discussed below, with more specific embodiments discussed in relation to FIGS. 4-10.

Figure 4:
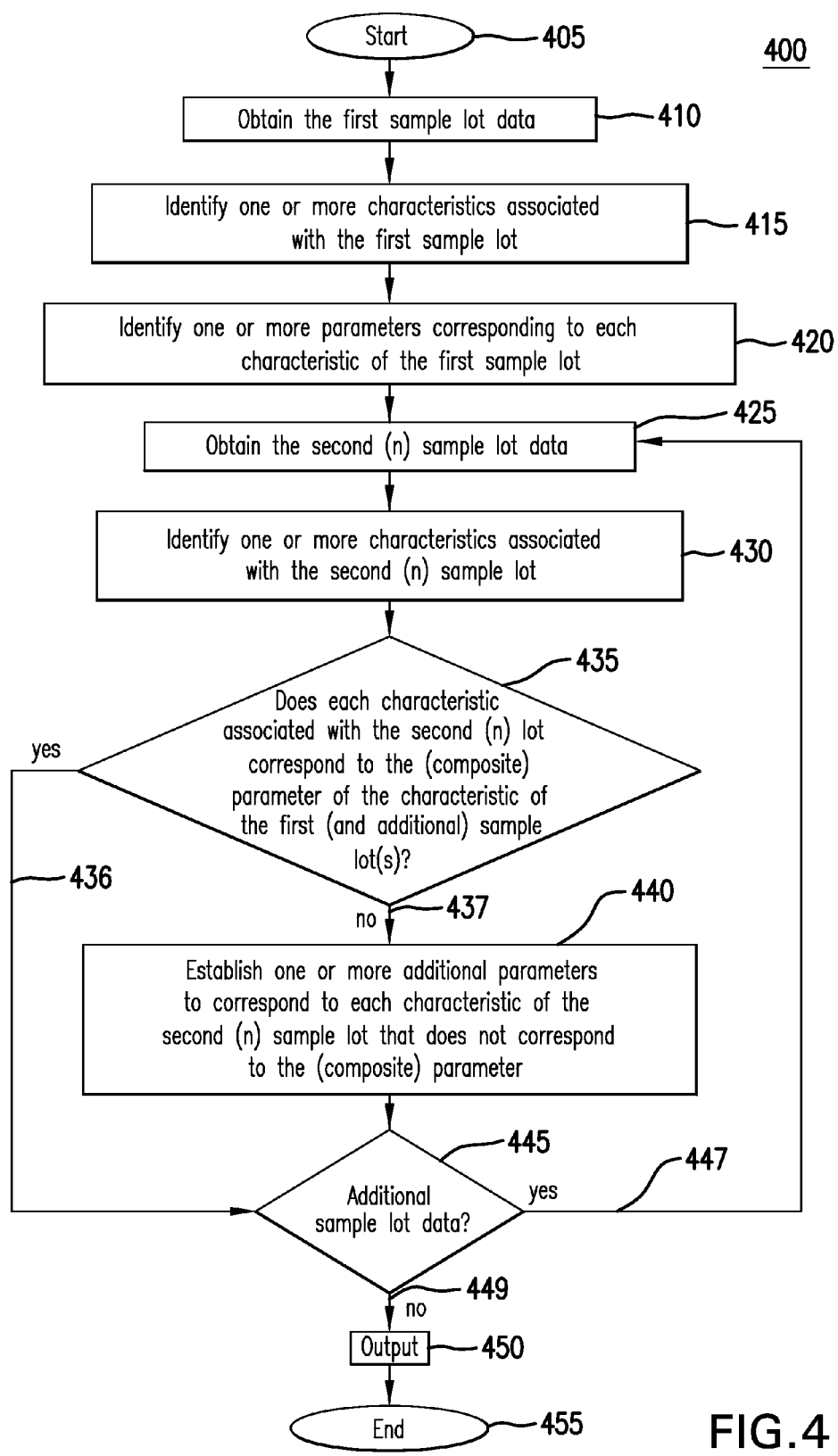
FIG. 4 is a flowchart of one embodiment of the present invention.

As shown in FIG. 4, algorithm 400 is a series of steps, typically stored on a computer-readable medium that may be executed at a server, client terminal, or other processing device to implement the present invention. Step 405 begins execution of the algorithm. Step 410 shows that the first sample lot data is obtained. It is an embodiment of this invention to apply this algorithm to a variety of data, the sample lot data could consist of, for example, chromatographic data for a particular complex biological, adjusted so that different sample lots may be compared to one another. The data may be received from a user terminal, web page, network device or other source of image data or sample data, and is typically transmitted over a network or other transmission medium. For example, data is obtained for a first sample, referred to herein as Lot A.

Step 415 shows that the characteristics associated with the first sample lot are identified. For chromatography data, the characteristics may be a function of the peaks with a specific relative retention time, found by the orthogonal techniques. Any suitable analytical means for characterizing components of the sample lot, however, also may be employed. In the example of Lot A, assume three characteristics are identified for Lot A: Point 1A=1.0 aum, Point 2A=2.0 aum, and Point 3A=3.0 aum.

Step 420 identifies the parameters corresponding to each characteristic of the first sample lot. The parameters may correspond to a one-dimensional space representation on an x-axis with an upper and lower boundary as a function of a predetermined mathematical relationship, forming a parameter set or parameter structure. With chromatographic peaks, the predetermined mathematical relationship may include determining the midpoints between the peaks from one lot to create the parameters. The parameters represent two boundary widths or "walls" on the x-axis (see FIG. 6G, which shows walls 605 and 646). These "walls" do not have to be shared by other parameters and typically do not overlap. Peaks are not located at the parameter if the walls are defined using more significant figures than the sample lot data. In the example, the parameters for Lot A would be:

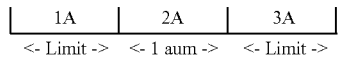

As another example, parameters may be established at the approximate mid-point between adjacent peaks in a sample lot. A multiplier such as 0.4999 is used instead of 0.5000, including a sufficient number of significant figures to prevent the parameters from overlapping. A sample lot contains, for example, three peaks where: Peak 1=0.452974 RRT, Peak 2=1.001994 RRT, and Peak 3=1.239947 RRT. The lower boundary wall for Peak 1=0.00001 (the default lower bin number for peak 1), and the upper boundary wall for Peak 1=Peak 1+(Peak 2−Peak 1)×0.4999=0.727429309 RRT. The lower boundary wall for Peak 2=Peak 2−(Peak 2−Peak 1)×0.4999=0.727539113 RRT, and the upper boundary wall for Peak 2=Peak 2+(Peak 3−Peak 2)×0.4999=1.120946633 RRT. The lower boundary wall for Peak 3=Peak 3−(Peak 3−Peak 2)×0.4999=1.120994223 RRT, and the upper boundary wall for Peak 3=50 (the default upper bin number for peak 3). The upper boundary wall of a peak may be fit closer to a subsequent peak by increasing the significant digits of the 0.4999 factor e.g., 0.4999999999999. In this example, the first peak lower boundary wall was set to 0.00001 by default, and the upper boundary wall was set to 50 by default. This is derived such that no peak will ever have a RRT smaller than 0.00001, and no peak will ever have an RRT larger than 50 in this example.

Second or subsequent (n) sample lot data is obtained in step 425. ("(n)" refers to additional sample lots e.g., 3, 4, 5 up to any suitable number) that may be obtained as the algorithm continues to process additional sample lots. Step 430 shows that the characteristics associated with the second sample lot data are identified. For example, assume four characteristics are identified for the second sample, Lot B: Point 1B=1.0 aum, Point 2B=2.0 aum, Point 3B=3.0 aum, and Point 4B=4.0 aum.

Step 435 determines whether each characteristic associated with the second or (n) sample lot corresponds to, or occupies, a composite parameter of the characteristic of the first (and additional) sample lot(s). The composite parameter is a result of matching points of Sample Lot B into the parameter established for Sample Lot A. If the answer to step 435 is "yes", line 436 leads to step 445; if the answer to step 435 is "no", line 437 leads to step 440. In the example, Lot B has a fourth, unique characteristic, Point 4B, which differs from the parameters established for Lot A, so the answer is "no", with line 437 leading to step 440.

Step 440 establishes the additional parameters to correspond to each characteristic of the second or (n) sample lot that does not correspond to the composite parameter. In the example, step 440 establishes a new parameter for the fourth characteristic represented by Point 4B below, with the following parameter structure:

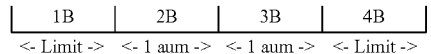

If we fit Lot A into the parameters of Lot B, Points 1, 2 and 3 are the same in both lots, but point 4 is unique to Lot B, resulting in the parameter structure:

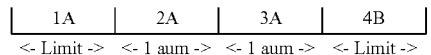

A parameter structure refers to the entire set of parameters associated with the sample lots. The initial parameter structure is a function of the parameters corresponding to each characteristic of the first sample lot. In the context of chromatographic peaks, for example, each peak will have its own parameters. Composite parameters are created when a new sample lot is fit into the existing parameters and the characteristics do not correspond to the existing parameters of the characteristic, causing the parameters to be restructured to new, composite parameters. Again, in the context of chromatographic peaks, this means that if more than one peak from the new lot (second or (n) lot) would fit in the existing parameters, the existing parameters would be restructured i.e., new parameters added and existing boundaries adjusted as necessary, to permit only one peak in the composite parameters from any individual lot.

The composite parameter structure is a dynamic iterative structure, because the parameter structure initially based on the first sample lot is continually being revised and restructured, as needed, to accommodate data from new sample lots. When the invention is used to analyze a specific type of product, including a complex biological such as pregnant mare's urine, the composite parameter structure typically becomes relatively stable after a sufficient number of sample lots have been analyzed and a significant portion of the characteristics or components correspond to the composite parameters. The composite parameter structure is also stable when there are no additional sample lots to analyze. After all characteristics associated with a second or (n) sample lot have been analyzed in this manner, the process proceeds to step 445.

As stated above, "yes" line 436 leads to step 445, which determines whether there are additional sample lot data to process. If the answer is "yes" line 447, then additional (n) sample lot data is processed, shown by step 425. In the example, the answer is "yes" and line 447 leads to step 425, which obtains data from a third sample, Lot C. Step 430 identifies four characteristics in Lot C: Point 1C=1.0 aum, Point 2C=1.1 aum, Point 3C=2.4 aum, and Point 4C=4.5 aum. Step 435 determines Lot C has two points, Points 1C and 2C, that are within the first parameter, and Points 3C and 4C have a somewhat different aum than lots A and B, so the answer is "no". If Points 1C and 2C were to remain in one parameter, this would mean that both characteristics are the same, and we know that they are not, because four separate characteristics were identified. This situation is represented by:

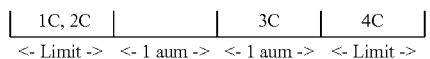

The answer "no" leads to line 437 and step 440. Step 440 establishes an additional parameter, so Points 1C and 2C each correspond to a parameter in composite parameter structure, which now encompasses Lots A, B, and C. If we fit Lot C into the composite parameter structure for Lots A, B, and C, the parameter structure would be:

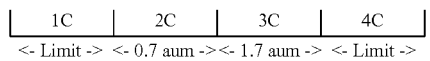

The results of this simplified process are summarized in the following table:

TABLE 1

| Bin # | Lot A aum | Lot B aum | Lot C aum | Low aum | High aum |
|---|---|---|---|---|---|
| | | | | Lot and high bin margins | |
| 1 | 1.0 | 1.0 | 1.0 | 0 (limit) | 1.05 |
| 2 | | | 1.1 | 1.05 | 1.75 |
| 3 | 2.0, 3.0 | 2.0, 3.0 | 2.4 | 1.75 | 3.45 |
| 4 | | 4.0 | 4.5 | 3.45 | 10 (limit) |

Table 1 demonstrates, however, that Lots A and B have two distinct points or characteristics, measured at 2.0 aum and 3.0 aum, which means step 440 establishes additional parameters to correspond to these characteristics, resulting in the following table:

TABLE 2

| Bin # | Lot A aum | Lot B aum | Lot C aum | Low aum | High aum |
|---|---|---|---|---|---|
| | | | | Lot and high bin margins | |
| 1 | 1.0 | 1.0 | 1.0 | 0 (limit) | 1.05 |
| 2 | | | 1.1 | 1.05 | 1.55 |
| 3 | 2.0 | 2.0 | | 1.55 | 2.2 |
| 4 | | | 2.4 | 2.2 | 2.7 |
| 5 | 3.0 | 3.0 | | 2.7 | 3.5 |
| 6 | | 4.0 | | 3.5 | 4.25 |
| 7 | | | 4.5 | 4.25 | 10 (limit) |

The array seen in Table 2 is the only arrangement of the data points that describes which points are similar and which points are unique. This embodiment of the data sorting invention is thus a dynamic iterative process that continuously fits new data points into the existing composite parameters thereby creating new composite parameters where all similar points are matched and unique points have their own parameters (lower and upper boundary).

If the answer to step 445 is "no" line 449, as in the example, shows an output step 450 is reached. In Output step 450 a representation as a function of the characteristics of the first sample lot, the characteristics of the second sample lot, as well as any subsequent sample lots, and the composite parameter structure, may be printed, displayed, transmitted to a location, such as a user terminal, other location designated by a user, or a memory coupled to the server, or processing device, executing algorithm 400. In the context of chromatographic peak data, output data may include a graphical or numerical representation. Two examples of output data that may be generated by the invention are included in FIGS. 9 and 10.

The algorithm ends, as shown in step 455.

Figure 5:
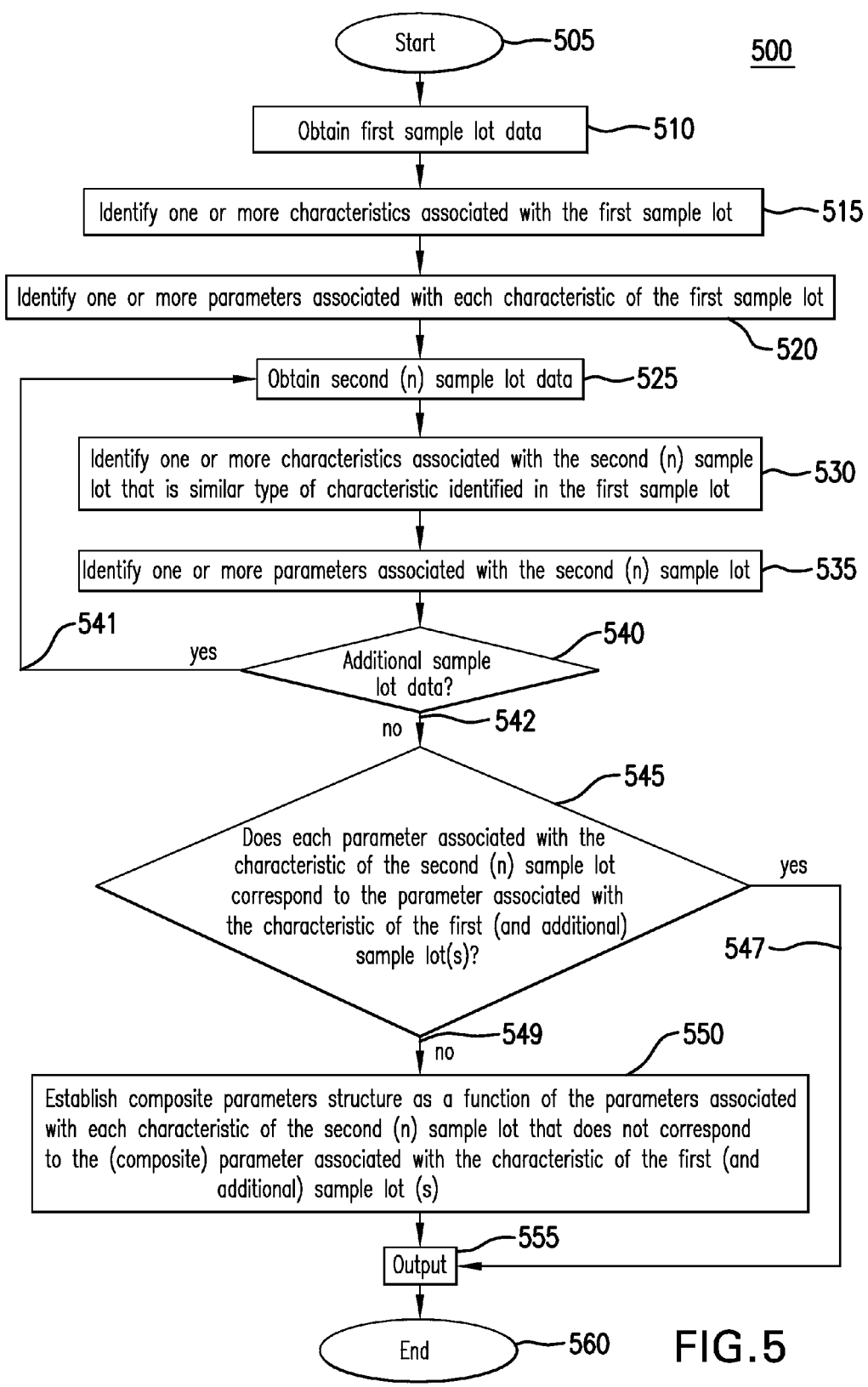
FIG. 5 is a flowchart of another embodiment of the present invention.

In FIG. 5, an alternate embodiment is shown using algorithm 500, which is a series of steps, typically stored on a computer-readable medium that may be executed at a server, or other processing device to implement the present invention. This embodiment is similar to the previous embodiment except that the composite parameters are established only after the parameters have been identified for all of the sample lots. The composite parameters that are established with this embodiment, however, are substantially similar to the parameter established using algorithm 400. This alternative embodiment may be preferred, however, depending on the data collection, processing methods, or apparatus employed.

Step 505 begins execution of the algorithm. The first sample lot data is obtained, as shown in step 510. Step 515 identifies the characteristics associated with the first sample lot. Step 520 identifies the parameters corresponding to each characteristic of the first sample lot. This establishes a parameter structure for the first sample lot.

The second or (n) (where (n) is any suitable number) sample lot data is obtained in step 525. Step 530 identifies the characteristics associated with the second (n) sample lot data that is a similar type of characteristic identified in the first sample lot. Step 535 identifies the parameters associated with the second or (n) sample lot, thereby creating parameters for the second or (n) sample lot data, which are independent of any other sample lot parameters. This establishes a parameter structure for the second or (n) sample lot. The characteristics associated with the second or (n) sample lot are typically a similar type of characteristic as the first sample lot, so the parameters associated with the characteristics correspond to the same data from the sample lots. For example, if the characteristic of the first sample lot is a function of a peak with a specific relative retention time, the characteristic of the second or (n) sample lot data would also be a function of a peak with a specific relative retention time. However, any analytical means for characterizing components in sample lot may be employed.

Step 540 determines whether there are additional sample lot data to process. If the answer is "yes", line 541 leads to step 525 in which additional (n) sample lot data are processed.

If the answer to step 540 is "no", line 542 leads to step 545 in which a determination is made whether each parameter associated with the characteristic of the second or (n) sample lot corresponds to the parameter associated with the characteristic of the first (and additional) sample lot(s). If the answer to step 545 is "yes", line 547, then leads to step 555; if the answer to step 545 is "no", line 549 leads to step is 550.

Step 550 establishes a composite parameter structure as a function of the parameters associated with each characteristic of the second or (n) sample lot that does not correspond to the composite parameter associated with the characteristic of the first and any additional sample lots.

The initial parameter structure is a function of the parameters corresponding to each characteristic of the first sample lot. The second or (n) parameter structure is a function of the parameters corresponding to each characteristic of the second or (n) sample lots, respectively. Composite parameters are created when the parameters associated with the characteristic of the second or (n) sample lot do not correspond to the initial parameter structure of the characteristic, causing the initial parameters to be restructured to new, composite parameters. In the context of chromatographic peaks, this means that the composite parameter structure should permit only one peak from each of the sample lots, where each peak corresponds to like compounds. After the composite parameter structure is completed for the new lot, the process moves to step 555.

Step 555 is the output, which is a representation as a function of the characteristics of the first sample lot, the characteristics of the second sample lot, and the composite parameter structure, may be printed, displayed, transmitted to a location, such as a user terminal, other location designated by a user, or a memory coupled to the server, or processing device, executing algorithm 500. Two examples of output data that may be generated by the invention are included in FIGS. 9 and 10.

The algorithm ends, as shown in step 560.

FIGS. 6A through 6H show representative sample lot data and parameters associated with elements for a substance with an unknown number of elements that have not been previously identified.

Figure 6A:
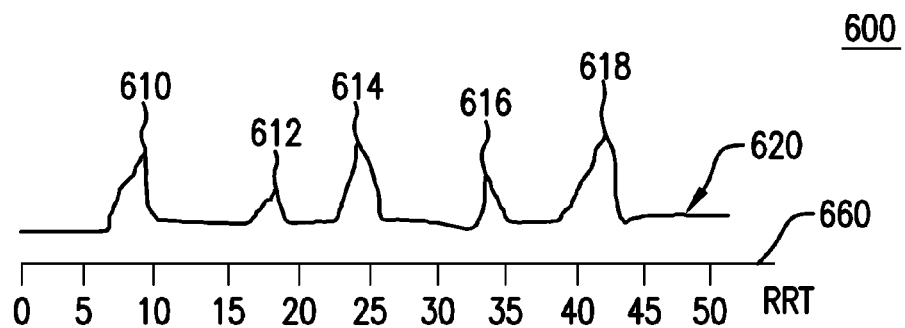
FIGS. 6A through 6H show a first example of representative sample lot data and parameters.

FIG. 6A is an example of the first sample lot data 620 for a substance, containing five unknown components with characteristics represented as peaks 610, 612, 614, 616, and 618. These peaks and all sample lots that will be illustrated in FIGS. 6A through 6H have been standardized to have relative retention times, represented by the scale 660.

Figure 6B:
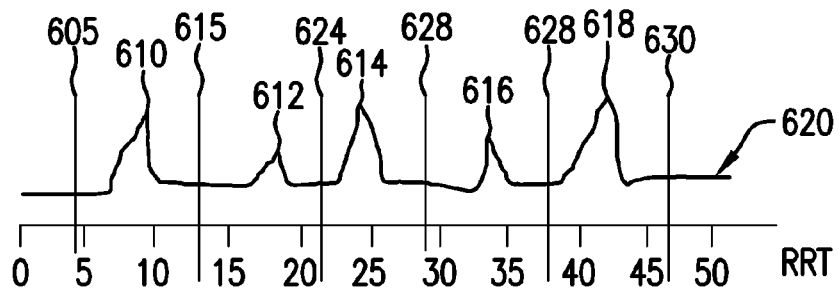

FIG. 6B shows an example of walls 605, 615, 624, 626, 628, 630 identified for characteristic peaks 610, 612, 614, 616, and 618. As previously explained, on an imaginary x-axis, a parameter consists of two boundary widths or "walls". While the walls do not have to be shared by other parameter sets, for ease of explanation in these and subsequent drawings, a parameter will be identified as having two subsequent walls and "composite walls" represent the walls associated with composite parameters.

Figure 6C:
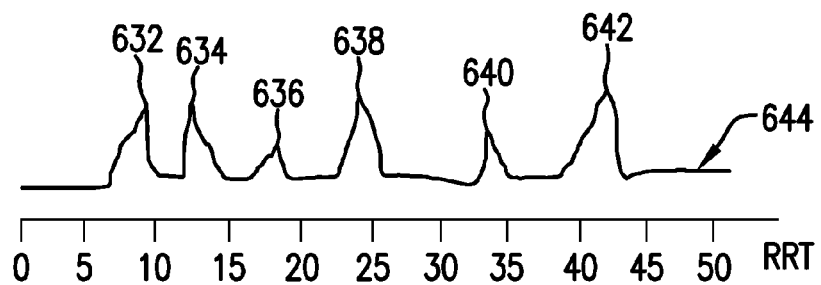

FIG. 6C is an example of the second lot data 644, containing six unknown components with characteristics represented as peaks 632, 634, 636, 638, 640, and 642.

Figure 6D:
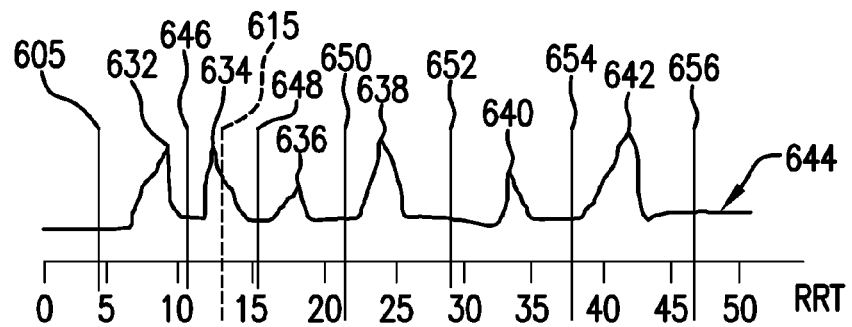

FIG. 6D shows an example of composite walls 605, 646, 648, 650, 652, 654, 656 identified for characteristic peaks 632, 634, 636, 638, 640, and 642. When sample lot data 644 was fit on the existing parameter structure for sample lot 1, shown in FIG. 6A, it was determined that the parameter with walls 605 and 615 now contained two characteristic peaks, 632 and 634. As a result, the initial parameter structure was restructured, removing wall 615, represented by a dashed line, and establishing the new, composite parameter structure. Also, a bin for peak 632 was added. This bin has walls 646 and 648.

Figure 6E:
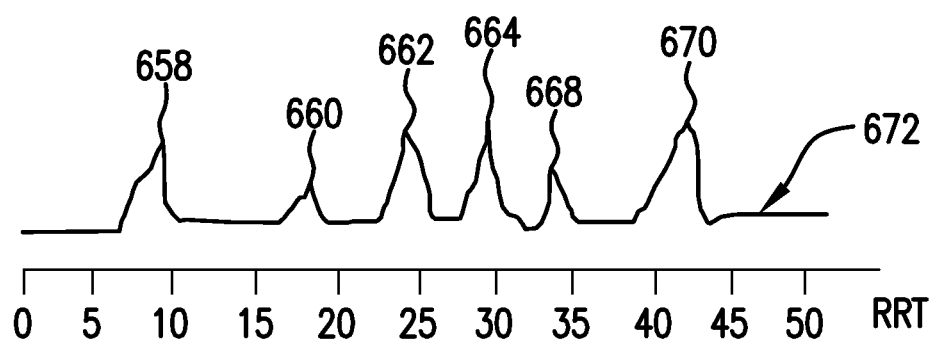

FIG. 6E is an example of the third lot data 672, containing six unknown components with characteristics represented as peaks 658, 660, 662, 664, 668, and 670.

Figure 6F:
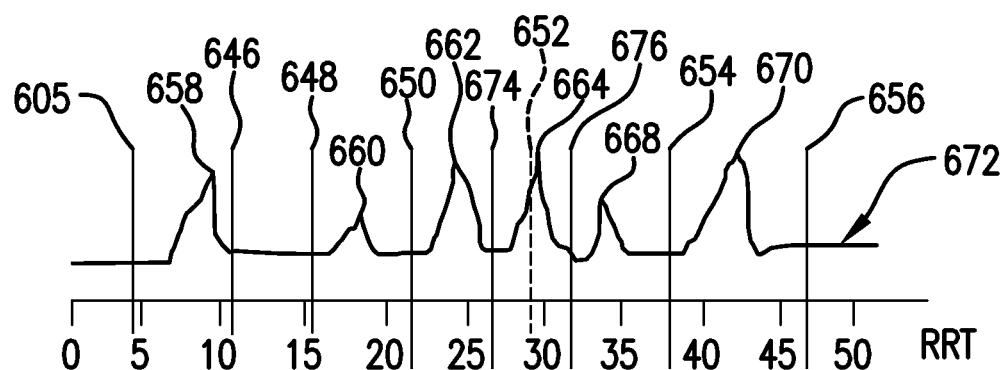

FIG. 6F shows an example of composite walls 605, 646, 648, 650, 674, 676, 654 and 656 identified for characteristic peaks 658, 660, 662, 664, 668, and 670. When sample lot data 672 was fit on the composite parameter structure for sample lots 1 and 2, it was determined that the parameter with walls 652 and 654 now contained two characteristic peaks, 664 and 668. As a result, the parameters were restructured, removing wall 652, represented by a dashed line, and establishing the new, composite parameter structure. While the parameter with walls 646 and 648 no longer contains a characteristic peak from sample lot data 672, it is retained for the composite parameter structure based on the sample lot 2 data 644.

Figure 6G:
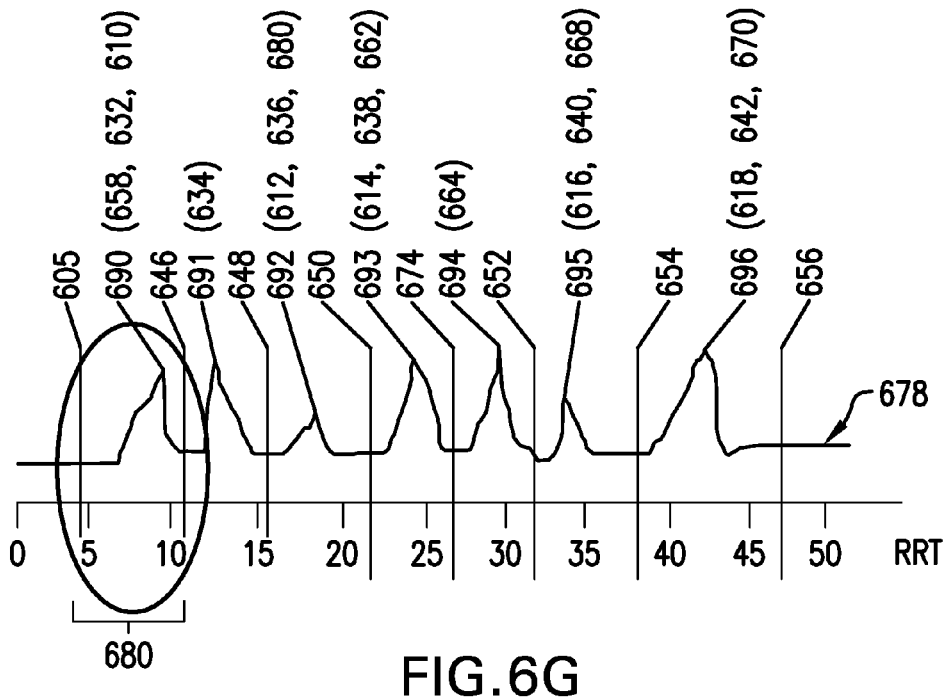

FIG. 6G shows and example of sample lot 1 620, sample lot 2 644, and sample lot 3 672 superimposed on one another forming data lot 678 with seven characteristic peaks, 690 (which is the same as 658, 632, 610), 691 (which is the same as 634), 692 (which is the same as 612, 636, 660), 693 (which is the same as 614, 638, 662), 694 (which is the same as 664), 695 (which is the same as 616, 640, 668), and 696 (which is the same as 618, 642, 670). This illustrates how the composite walls 605, 646, 648, 650, 674, 652, 654, and 656 permit only one peak for each parameter.

Figure 6H:
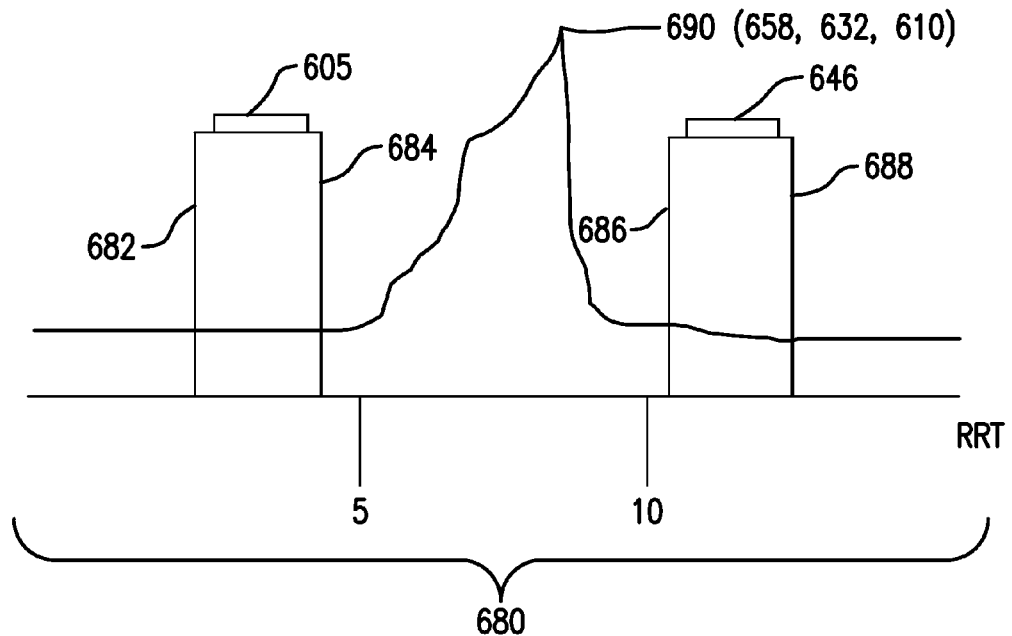

FIG. 6H is an enlargement of the selected portion 680 of FIG. 6G, showing the composite parameter with walls 605 and 646. For peak 690 (which is the same as 658, 632, 610), the walls 605 and 646 have been enlarged to reveal the upper and lower boundary for each wall. To prevent characteristics from occurring at a wall, as previously noted, the walls will generally be defined with more significant figures than the sample lot data. Wall 605 has a lower boundary represented by 682 and an upper boundary represented by 684. Wall 646 has a lower boundary 686 and an upper boundary 688. The peak 690, is disposed between walls 605 and 646.

FIGS. 7A through 7G show representative sample lot data and parameters associated with elements for a substance with an unknown number of elements that have not been previously identified. FIGS. 7A-7G illustrate an embodiment of the invention in which sample lots are processed and a composite parameter structure is then generated.

Figure 7A:
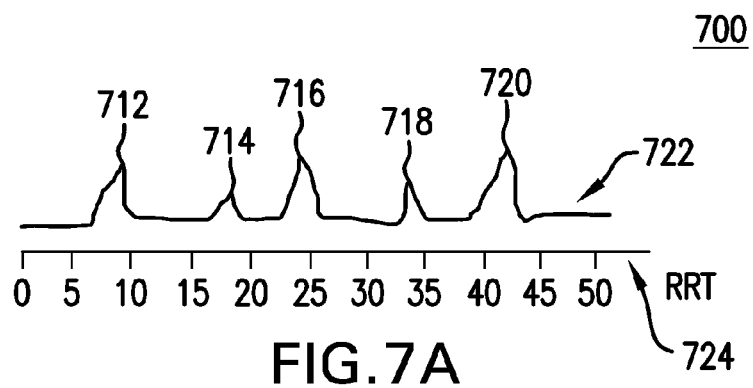
FIGS. 7A through 7G show a second example of representative sample lot data and parameters.

FIG. 7A is an example of the first sample lot data 722 for a substance, containing five unknown components with characteristics represented as peaks 712, 714, 716, 718, and 720. These peaks and all sample lots that will be illustrated in FIGS. 7A through 7G typically have been standardized to have relative retention times, represented by the scale 724.

Figure 7B:
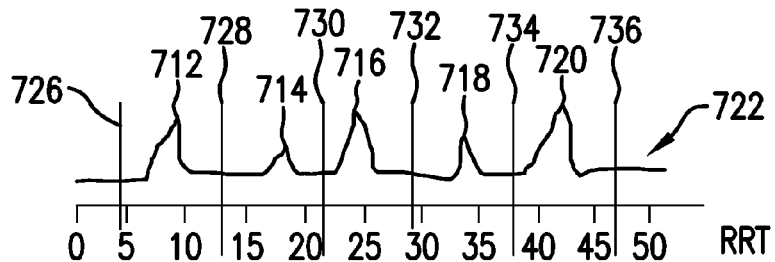

FIG. 7B shows an example of walls 726, 728, 730, 732, 734, 736 identified for characteristic peaks 712, 714, 716, 718, and 720.

Figure 7C:
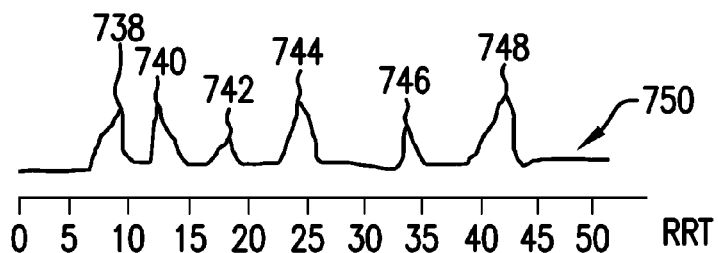

FIG. 7C is an example of the second lot data 750, containing six unknown components with characteristics represented as peaks 738, 740, 742, 744, 746, and 748.

Figure 7D:
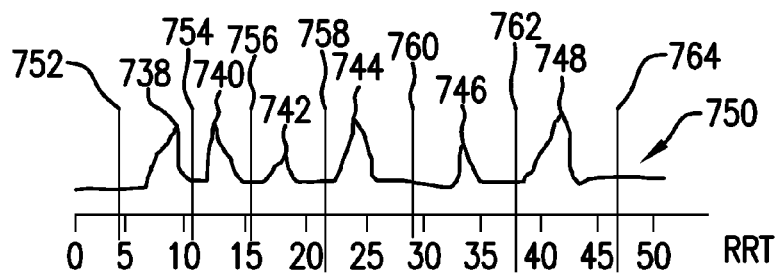

FIG. 7D shows an example of walls 752, 754, 756, 758, 760, 762, and 764 identified for characteristic peaks 738, 740, 742, 744, 746, and 748 for the second sample lot data 750.

Figure 7E:
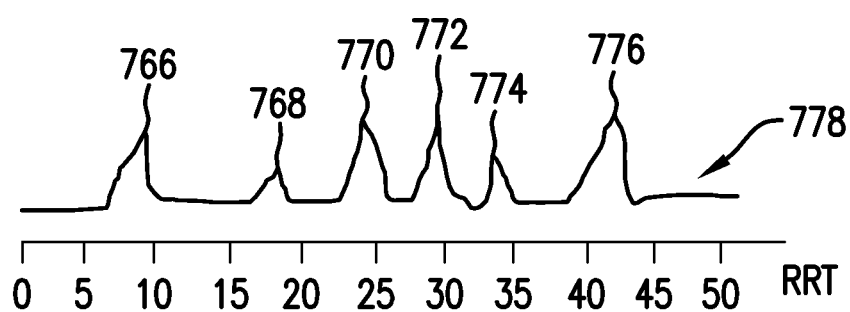

FIG. 7E is an example of the third lot data 778, containing six unknown components with characteristics represented as peaks 766, 768, 770, 772, 774, and 776.

Figure 7F:
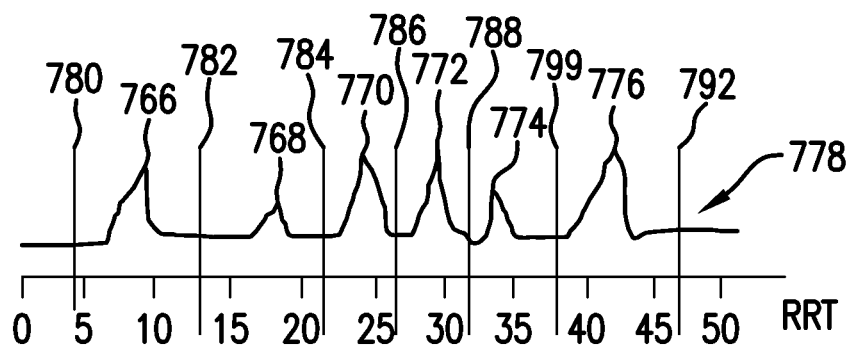

FIG. 7F shows an example of walls 780, 782, 784, 786, 788, 790, and 792 identified for characteristic peaks 766, 768, 770, 772, 774, and 776.

Figure 7G:
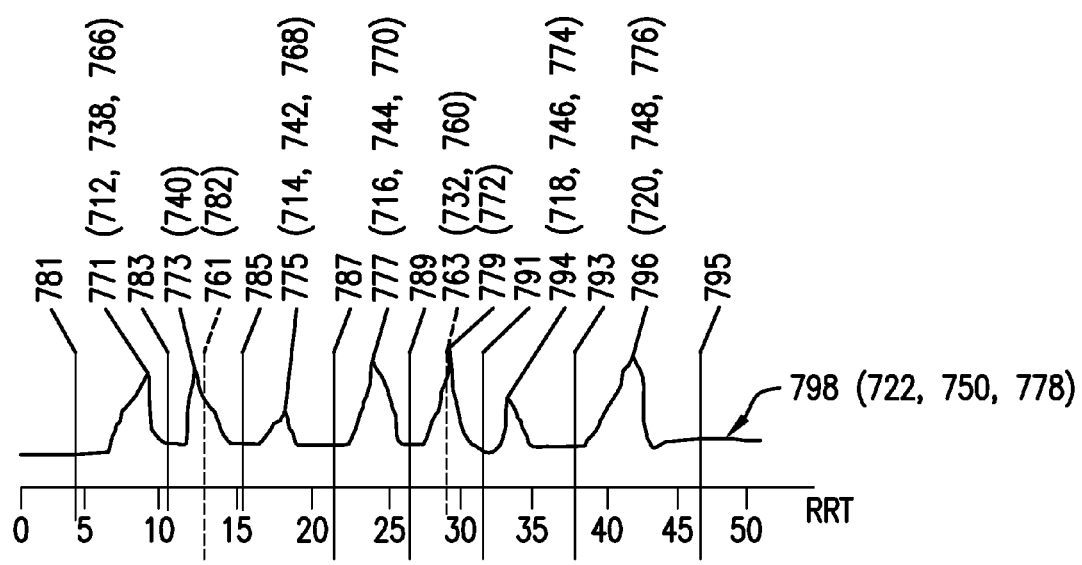

FIG. 7G shows and example of sample lot 1 722, sample lot 2 750, and sample lot 3 778 superimposed on one another forming data lot 798 with seven characteristic peaks, 771 (which is the same as 712, 738, 766), 773 (which is the same as 740), 775 (which is the same as 714, 742, 768), 777 (which is the same as 716, 744, 770), 779 (which is the same as 772), 794 (which is the same as 718, 746, 774), and 796 (which is the same as 720, 748, 776). This illustrates how the composite walls 781, 783, 785, 787, 789, 791, 793, 795 permit only one peak for each parameter. When it was determined whether each parameter associated with characteristic peaks of sample lot data 722, 750, and 778 corresponded to the parameter associated with the characteristic of the first (and additional) sample lots, the composite walls were restructured to remove walls 761 (which is the same as 782) and 763 (which is the same as 732, 760), which are both represented by a dashed line. This illustrates how the composite walls permit only one peak for each parameter.

Figure 8:
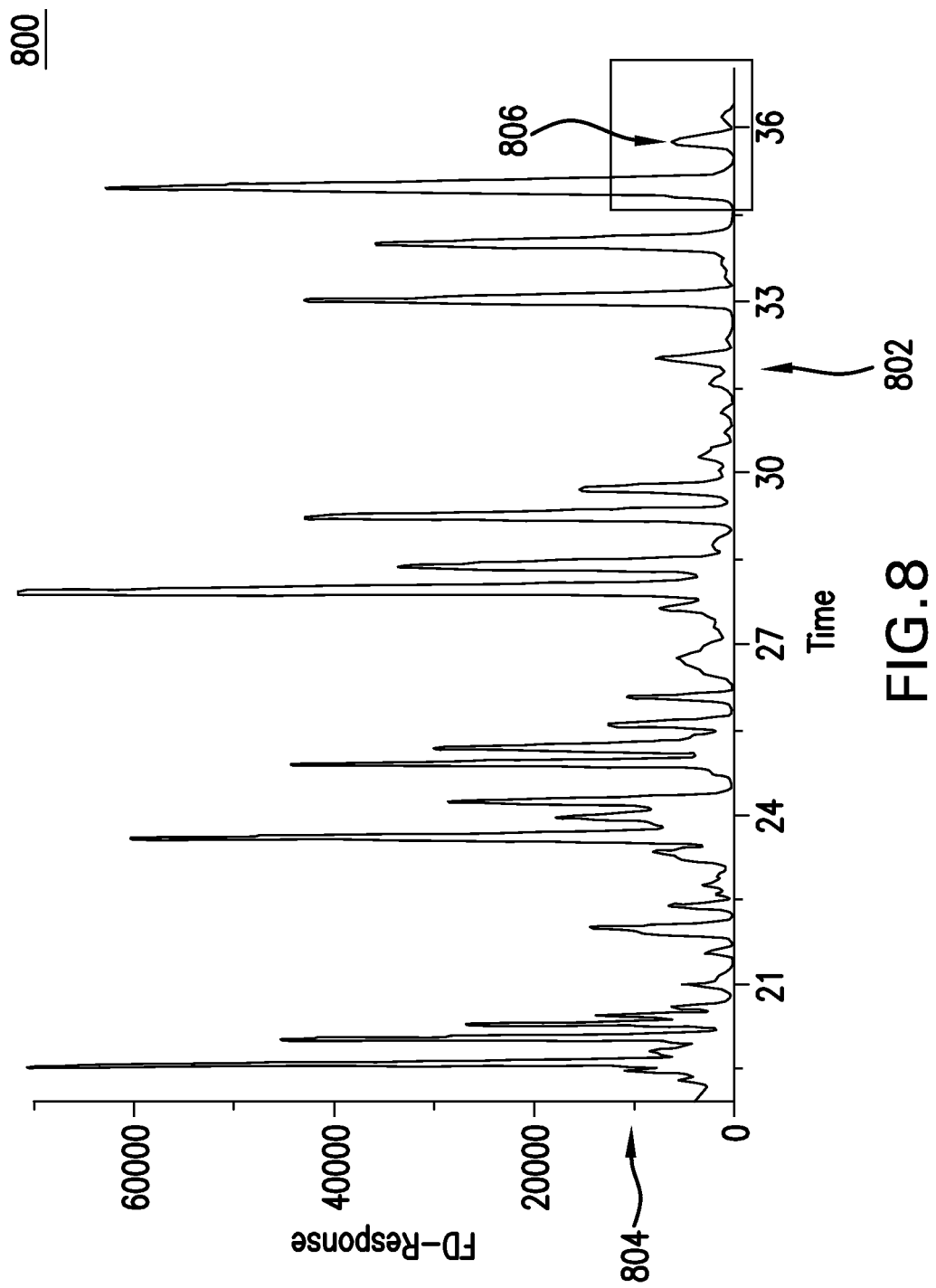
FIG. 8 shows an example of a sample lot using the present invention.

FIG. 8 shows the representative sample lot 800 data from a chromatogram with many characteristics associated with unknown components that could be sorted using the methods claimed herein. Axis 802 shows the relative retention time with characteristic peaks, such as peak 806. Axis 804 shows the intensity of the characteristic RT peaks, noted as an "FID-Response", which utilizes a chromatographic method with a flame ionization detector (FID) to characterize the components in a complex composition.

Figure 9:
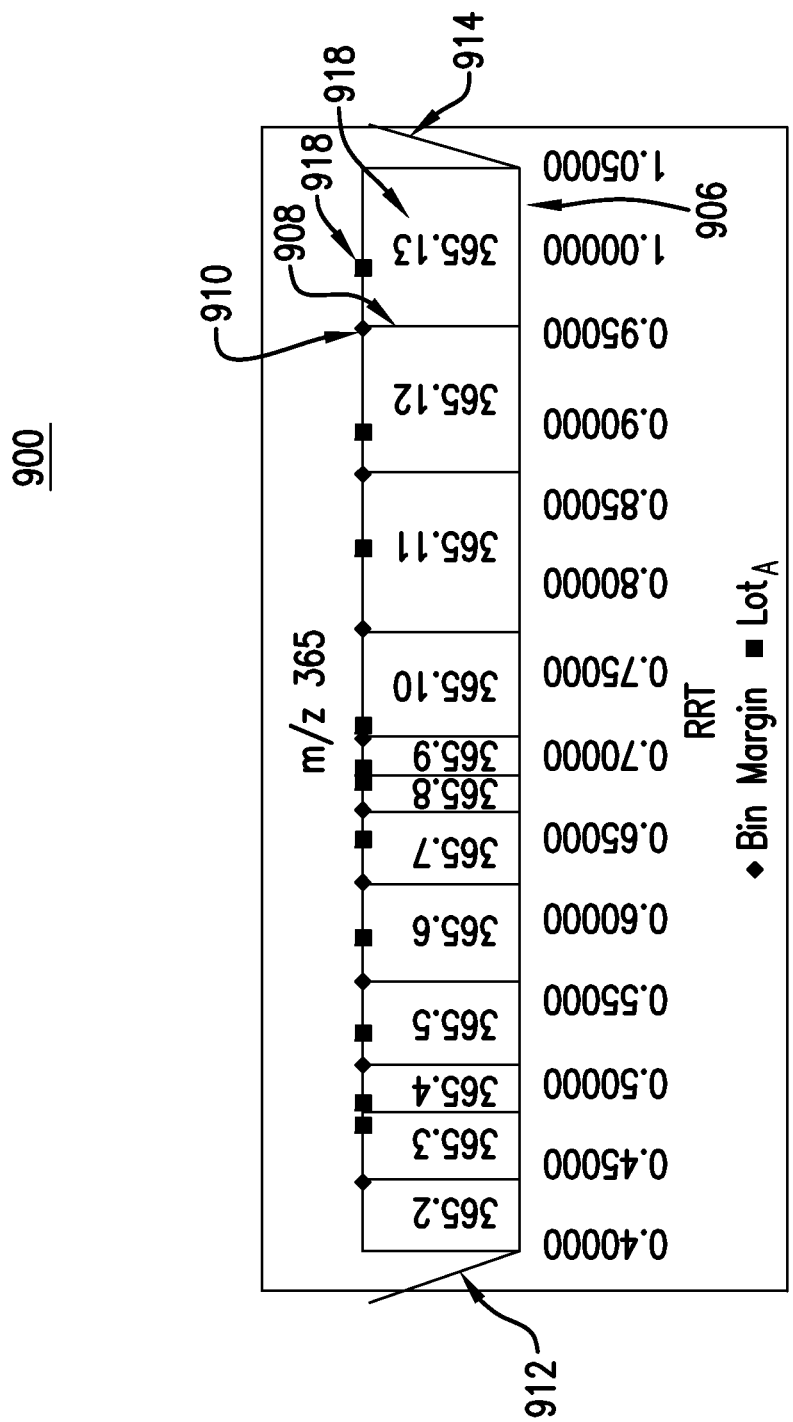
FIG. 9 shows a graph output generated by the invention.

FIG. 9 shows a graph output 900 generated by the invention comparing a sample lot A with an atomic mass (m/z) of 365 to the composite parameter generated as described in the invention from multiple sample lots with similar m/z values. For this example, the data was obtained from a separation technique that separates the compound by atomic mass (m/z) and an orthogonal technique, such as column chromatography. The retention time of the column was adjusted with a quantitative standard to provide a relative retention time (RRT) 906 to compare between sample lots and the specific m/z values 918. The RRT values for sample Lot A are indicated as square markers 916, and the composite parameters that were identified or established by the invention from all of the sample lots are indicated with diamond markers 910 and lines 908. As shown in this output, while each characteristic RRT will correspond to a single composite parameter, the composite parameters are not necessarily uniform in size, and each characteristic is not necessarily found in the center of a composite parameter, even if, as with sample Lot A, this was initially the case, when the parameters were established roughly halfway between each of the RRT values for the first sample lot. The lowest and highest parameters, 912 and 914 respectively, are slanted outward to represent a function that will catch the expected lowest and highest RRTs from future sample lots. In general, the parameters should never overlap, as illustrated in FIG. 6H.

FIG. 10 shows a table output 1000 generated by the invention, which was obtained in the similar manner as FIG. 9, for two different sample Lots A and B with an atomic mass (m/z) value of 365. Each of the successive RRT values is numbered sequentially with a characteristic number. The upper and lower boundaries for the identified parameters are initially established roughly halfway between each of the RRT values, where a multiplier such as 0.4999 is used instead of 0.5000, including a sufficient number of significant figures to prevent the parameters from overlapping. As with FIG. 9, while each characteristic RRT will correspond to a single composite parameter, the composite parameters are not necessarily uniform in size, and each characteristic is not necessarily found in the center of a composite parameter, even if, as with Lot A, this was initially the case, when the parameters were established roughly halfway between each of the RRT values. This table also shows that the default lowest boundary was set at 0 and the default highest boundary was set at 50, to capture all of the RRT values within the two sample lots in this example.

An apparatus comprising:
means for identifying one or more characteristics associated with a first sample lot;
means for identifying parameters corresponding to each of the one or more characteristics of the first sample lot;
means for identifying one or more characteristics associated with a second sample lot;
means for determining whether the one or more characteristics associated with the second sample lot correspond to one or more of the parameters corresponding to the characteristic of the first sample lot; and
means for establishing one or more additional parameters corresponding to each characteristic of the second sample lot that does not correspond to the parameters corresponding to the characteristic of the first sample lot.

The apparatus of above, further comprising a means for establishing a composite parameter structure (dynamic iterative structure) as a function of the parameters corresponding to characteristics of the first sample lot and the additional parameters.

The apparatus of above, further comprising a means for generating a representation as a function of the characteristics of the first sample lot, the characteristics of the second sample lot, and the composite parameter structure (dynamic iterative structure).

The apparatus of above, further comprising a means for modifying one or more boundaries of the composite parameter structure as a function of the one or more characteristics associated with the first sample lot and the second sample lot.

The apparatus of above, wherein means for the characteristics are a function of a relative retention time.

The apparatus of above, wherein means for the one or more boundaries are a function of a predetermined mathematical relationship.

The apparatus of above, further comprising:
means for identifying one or more characteristics associated with a third sample lot;
means for determining whether the one or more characteristics associated with the third sample lot correspond to one or more parameters of the composite parameter structure.

The apparatus of above, further comprising a means for modifying the composite parameter structure as a function of characteristics of the third sample lot.

The apparatus of above, further comprising:
means for identifying one or more characteristics associated with an $n^{th}$-sample lot;
means for determining whether the one or more characteristics associated with the $n^{th}$-sample lot correspond to one or more parameters of the composite structure.

The apparatus of above, wherein means for the characteristics are a function of one or more peaks.

The apparatus of above, wherein means for each peak is a function of a relative retention time.

The apparatus of above, wherein means for each parameter is defined as a mathematical quantity.

The apparatus of above, wherein means for each parameter has an upper boundary and a lower boundary.

The apparatus of above, wherein means for the determining step includes assigning one or more compounds to selected parameters.

The apparatus of above, wherein means for each sample lot will have one or more characteristics corresponding to a parameter.

The apparatus of above, wherein means for when the step of identifying one or more characteristics associated with a second sample lot identifies that more than one characteristic from the first sample lot exists in any one parameter, the parameters are restructured such that no more than one characteristic from a sample lot corresponds to a particular parameter.

The apparatus of above, wherein means for characteristics in a particular parameter originate from different sample lots.

The apparatus of above, wherein means for characteristics in a particular parameter correspond to the same entity.

An apparatus comprising:
means for identifying one or more characteristics associated with a first sample lot;
means for identifying one or more parameters associated with the characteristics of the first sample lot;
means for identifying one or more characteristics associated with a second sample lot that is a similar type of characteristic identified in the first sample lot;
means for identifying one or more parameters associated with the characteristics of the second sample lot;
means for determining whether the one or more parameters associated with the characteristics of the second sample lot corresponds to the one or more parameters associated with the characteristics of the first sample lot;
means for establishing a composite parameter structure as a function of the parameters associated with the characteristics of the first sample lot and the parameters associated with the characteristics of the second sample lot.

The apparatus of above, further comprising means for generating a representation as a function of the characteristics of the first sample lot, the characteristics of the second sample lot, and the composite parameter structure.

The apparatus of above, further comprising:
means for identifying one or more characteristics associated with an $n^{th}$-sample lot;
means for identifying one or more parameters associated with the characteristics of the $n^{th}$-sample lot;
means for establishing the composite parameter structure as a function of the one or more parameters associated with the characteristics of the first sample lot, the one or more parameters associated with characteristics of the second sample lot, and one or more parameters associated with the characteristics of the $n^{th}$-sample lot.

The apparatus of above, further comprising means for modifying one or more boundaries of the composite parameter structure as a function of the characteristics of the first sample lot and the second sample lot.

The apparatus of above, wherein means for the characteristics are a function of a relative retention time.

The apparatus of above, wherein means for the characteristics are a function of one or more peaks.

The apparatus of above, wherein means for each peak is a function of a relative retention time.

The apparatus of above, wherein means for each sample lot will have one or more characteristics corresponding to a parameter.

A method comprising:
means for identifying one or more characteristics associated with a first sample lot;
means for identifying parameters corresponding to each of the one or more characteristics of the first sample lot;
means for identifying one or more characteristics associated with a second sample lot;
means for determining whether the one or more characteristics associated with the second sample lot correspond to one or more of the parameters corresponding to the characteristic of the first sample lot; and
means for establishing one or more additional parameters corresponding to each characteristic of the second sample lot that does not correspond to the parameters corresponding to the characteristic of the first sample lot.

The method of above, further comprising means for establishing a composite parameter structure (dynamic iterative structure) as a function of the parameters corresponding to characteristics of the first sample lot and the additional parameters.

The method of above, further comprising means for generating a representation as a function of the characteristics of the first sample lot, the characteristics of the second sample lot, and the composite parameter structure (dynamic iterative structure).

The method of above, further comprising means for modifying one or more boundaries of the composite parameter structure as a function of the one or more characteristics associated with the first sample lot and the second sample lot.

The method of above, wherein means for the characteristics are a function of a relative retention time.

The method of above, wherein means for the one or more boundaries are a function of a predetermined mathematical relationship.

The method of above, further comprising:
means for identifying one or more characteristics associated with a third sample lot;
means for determining whether the one or more characteristics associated with the third sample lot correspond to one or more parameters of the composite parameter structure.

The method of above, further comprising means for modifying the composite parameter structure as a function of characteristics of the third sample lot.

The method of above, further comprising:
means for identifying one or more characteristics associated with an $n^{th}$-sample lot;
means for determining whether the one or more characteristics associated with the $n^{th}$-sample lot correspond to one or more parameters of the composite structure.

The method of above, wherein means for the characteristics are a function of one or more peaks.

The method of above, wherein means for each peak is a function of a relative retention time.

The method of above, wherein means for each parameter is defined as a mathematical quantity.

The method of above, wherein means for each parameter has an upper boundary and a lower boundary.

The method of above, wherein means for the determining step includes assigning one or more compounds to selected parameters.

The steps of above, wherein means for each sample lot will have one or more characteristics corresponding to a parameter.

The method of above, wherein means for when the step of identifying one or more characteristics associated with a second sample lot identifies that more than one characteristic from the first sample lot exists in any one parameter, the parameters are restructured such that no more than one characteristic from a sample lot corresponds to a particular parameter.

The method of above, wherein means for characteristics in a particular parameter originate from different sample lots.

The method of above, wherein means for characteristics in a particular parameter correspond to the same entity.

A method comprising:
means for identifying one or more characteristics associated with a first sample lot;
means for identifying one or more parameters associated with the characteristics, of the first sample lot;
means for identifying one or more characteristics associated with a second sample lot that is a similar type of characteristic identified in the first sample lot;

means for identifying one or more parameters associated with the characteristics of the second sample lot;

means for determining whether the one or more parameters associated with the characteristics of the second sample lot corresponds to the one or more parameters associated with the characteristics of the first sample lot;

establishing a composite parameter structure as a function of the parameters associated with the characteristics of the first sample lot and the parameters associated with the characteristics of the second sample lot.

The method of above, further comprising means for generating a representation as a function of the characteristics of the first sample lot, the characteristics of the second sample lot, and the composite parameter structure.

The method of above, further comprising:

means for identifying one or more characteristics associated with an $n^{th}$-sample lot;

means for identifying one or more parameters associated with the characteristics of the $n^{th}$-sample lot;

means for establishing the composite parameter structure as a function of the one or more parameters associated with the characteristics of the first sample lot, the one or more parameters associated with characteristics of the second sample lot, and one or more parameters associated with the characteristics of the $n^{th}$-sample lot.

The method of above, further comprising means for modifying one or more boundaries of the composite parameter structure as a function of the characteristics of the first sample lot and the second sample lot.

The method of above, wherein means for the characteristics are a function of a relative retention time.

The method of above, wherein means for the characteristics are a function of one or more peaks.

The method of above, wherein means for each peak is a function of a relative retention time.

The method of above, wherein means for each sample lot will have one or more characteristics corresponding to a parameter.

A processing apparatus comprising:
at least one memory; and
a processor, coupled to the at least one memory adapted to execute program code to:
identify one or more characteristics associated with a first sample lot;
identify parameters corresponding to each of the one or more characteristics of the first sample lot;
identify one or more characteristics associated with a second sample lot;
determine whether the one or more characteristics associated with the second sample lot correspond to one or more of the parameters corresponding to the characteristic of the first sample lot; and
establish one or more additional parameters corresponding to each characteristic of the second sample lot that does not correspond to the parameters corresponding to the characteristic of the first sample lot.

The processing apparatus of above, further comprising a processor, coupled to the at least one memory adapted to execute program code to establish a composite parameter structure (dynamic iterative structure) as a function of the parameters corresponding to characteristics of the first sample lot and the additional parameters.

The processing apparatus of above, further comprising a processor, coupled to the at least one memory adapted to execute program code to generate a representation as a function of the characteristics of the first sample lot, the characteristics of the second sample lot, and the composite parameter structure (dynamic iterative structure).

The processing apparatus of above, further comprising a processor, coupled to the at least one memory adapted to execute program code to modify one or more boundaries of the composite parameter structure as a function of the one or more characteristics associated with the first sample lot and the second sample lot.

The processing apparatus of above, wherein the characteristics are a function of a relative retention time.

The processing apparatus of above, wherein the one or more boundaries are a function of a predetermined mathematical relationship.

The processing apparatus of above, further comprising a processor, coupled to the at least one memory adapted to execute program code to:
identify one or more characteristics associated with a third sample lot;
determine whether the one or more characteristics associated with the third sample lot correspond to one or more parameters of the composite parameter structure.

The processing apparatus of above, further comprising a processor, coupled to the at least one memory adapted to execute program code to modify the composite parameter structure as a function of characteristics of the third sample lot.

The processing apparatus of above, further comprising a processor, coupled to the at least one memory adapted to execute program code to:
identify one or more characteristics associated with an $n^{th}$-sample lot;
determine whether the one or more characteristics associated with the $n^{th}$-sample lot correspond to one or more parameters of the composite structure.

The processing apparatus of above, wherein the characteristics are a function of one or more peaks.

The processing apparatus of above, wherein each peak is a function of a relative retention time.

The processing apparatus of above, wherein each parameter is defined as a mathematical quantity.

The processing apparatus of above, wherein each parameter has an upper boundary and a lower boundary.

The processing apparatus of above, wherein the processor, coupled to the at least one memory adapted to execute program code includes the determining step to assign one or more compounds to selected parameters.

The processing apparatus of above, wherein each sample lot will have one or more characteristics corresponding to a parameter.

The processing apparatus of above, wherein when the processor, coupled to the at least one memory adapted to execute program code to identify one or more characteristics associated with a second sample lot identifies that more than one characteristic from the first sample lot exists in any one parameter, the parameters are restructured such that no more than one characteristic from a sample lot corresponds to a particular parameter.

The processing apparatus of above, wherein characteristics in a particular parameter originate from different sample lots.

The processing apparatus of above, wherein characteristics in a particular parameter correspond to the same entity.

A processing apparatus comprising:
at least one memory; and
a processor, coupled to the at least one memory adapted to execute program code to:
identify one or more characteristics associated with a first sample lot;

identify one or more parameters associated with the characteristics of the first sample lot;

identify one or more characteristics associated with a second sample lot that is a similar type of characteristic identified in the first sample lot;

identify one or more parameters associated with the characteristics of the second sample lot;

determine whether the one or more parameters associated with the characteristics of the second sample lot corresponds to the one or more parameters associated with the characteristics of the first sample lot;

establish a composite parameter structure as a function of the parameters associated with the characteristics of the first sample lot and the parameters associated with the characteristics of the second sample lot.

The processing apparatus of above, further comprising a processor, coupled to the at least one memory adapted to execute program code to generate a representation as a function of the characteristics of the first sample lot, the characteristics of the second sample lot, and the composite parameter structure.

The processing apparatus of above, further comprising a processor, coupled to the at least one memory adapted to execute program code to:

identify one or more characteristics associated with an $n^{th}$-sample lot;

identify one or more parameters associated with the characteristics of the $n^{th}$-sample lot;

establish the composite parameter structure as a function of the one or more parameters associated with the characteristics of the first sample lot, the one or more parameters associated with characteristics of the second sample lot, and one or more parameters associated with the characteristics of the $n^{th}$-sample lot.

The processing apparatus of above, further comprising a processor, coupled to the at least one memory adapted to execute program code to modify one or more boundaries of the composite parameter structure as a function of the characteristics of the first sample lot and the second sample lot.

The processing apparatus of above, wherein the characteristics are a function of a relative retention time.

The processing apparatus of above, wherein the characteristics are a function of one or more peaks.

The method of above, wherein each peak is a function of a relative retention time.

The method of above, wherein each sample lot will have one or more characteristics corresponding to a parameter.

Thus, while fundamental novel features of the invention shown and described and pointed out, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in another form or embodiment. It is the intention, therefore, to be limited only as indicated by the scope of the claims appended hereto.

What is claimed is:

1. A method for sorting chromatographic data comprising:
(a) providing chromatographic data related to a first sample lot and chromatographic data related to a second sample lot to a processor;
(b) using the processor to identify one or more chromatographic peaks associated with the first sample lot;
(c) using the processor to identify parameters corresponding to each of the one or more chromatographic peaks of the first sample lot;
(d) using the processor to identify one or more chromatographic peaks associated with the second sample lot;
(e) using the processor to determine whether the one or more chromatographic peaks associated with the second sample lot correspond to one or more of the parameters corresponding to the chromatographic peaks of the first sample lot;
(f) using the processor to establish one or more additional parameters corresponding to each chromatographic peak of the second sample lot that does not correspond to the parameters corresponding to the chromatographic peaks of the first sample lot;
(g) using the processor to provide the additional parameters to an output device; and
(h) using the processor to establish a composite parameter structure as a function of the parameters corresponding to the chromatographic peaks of the first sample lot and only one chromatographic peak corresponding to each of the additional parameters.

2. The method of claim 1, wherein each peak is a function of a relative retention time.

3. The method of claim 1, further comprising using the processor to generate a representation as a function of the first sample lot, the chromatographic peaks of the second sample lot, and the composite parameter structure.

4. The method of claim 1, further comprising: identifying one or more chromatographic peaks associated with a third sample lot; and determining whether the one or more chromatographic peaks associated with the third sample lot correspond to one or more parameters of the composite parameter structure.

5. The method of claim 4, further comprising modifying the composite parameter structure as a function of chromatographic peaks of the third sample lot.

6. The method of claim 1, further comprising: identifying one or more chromatographic peaks associated with an $n^{th}$-sample lot; and determining whether the one or more chromatographic peaks associated with the $n^{th}$-sample lot correspond to one or more parameters of the composite structure.

7. A method for determining whether the chemical composition of a generic formulation of pregnant mare's urine corresponds to that of a reference listed drug comprising conjugated estrogens, the method comprising:
(a) creating a composite parameter structure corresponding to the reference listed drug by:
(i) providing data related to a first sample lot of the reference listed drug and data related to a second sample lot of the reference listed drug to a processor;
(ii) using the processor to identify one or more characteristics associated with the first sample lot;
(iii) using the processor to identify parameters corresponding to each of the one or more characteristics of the first sample lot;
(iv) using the processor to identify one or more characteristics associated with the second sample lot;
(v) using the processor to determine whether the one or more characteristics associated with the second sample lot correspond to one or more of the parameters corresponding to the characteristic of the first sample lot;
(vi) using the processor to establish one or more additional parameters corresponding to each characteristic of the second sample lot that does not correspond to the parameters corresponding to the characteristic of the first sample lot;
(vii) using the processor to provide the additional parameters to an output device; and
(viii) using the processor to establish the composite parameter structure as a function of the parameters corresponding to characteristics of the first sample lot and only one chromatographic peak corresponding to each of the additional parameters;
(b) comparing data related to at least one sample lot of the generic formulation to the composite parameter structure; and
(c) determining whether the chemical composition of the generic formulation corresponds to that of the reference listed drug based on the comparison in step (b).

8. The method of claim 7, wherein at least one of the characteristics is a function of a relative retention time.

9. The method of claim 7, wherein at least one of the characteristics is a function of atomic mass units.

10. The method of claim 7, wherein at least one of the characteristics is a function of one or more peaks.

11. The method of claim 10, wherein each peak is a function of a relative retention time.

12. A processing apparatus comprising a server, a network, and a client terminal, wherein:
the server comprises at least one memory, a processor, and at least one circuit; the server is adapted to transmit data to and receive data from the client terminal, via the network;
the processor is operatively connected to the memory and the circuit; and
the processor is adapted to execute program code to:
identify one or more characteristics associated with the first sample lot;
identify parameters corresponding to each of the one or more characteristics of the first sample lot;
identify one or more characteristics associated with the second sample lot;
determine whether the one or more characteristics associated with the second sample lot correspond to one or more of the parameters corresponding to the characteristic of the first sample lot;
establish one or more additional parameters corresponding to each characteristic of the second sample lot that does not correspond to the parameters corresponding to the characteristic of the first sample lot;
provide the additional parameters to an output device; and
establish a composite parameter structure as a function of the parameters corresponding to characteristics of the first sample lot and only one chromatographic peak corresponding to each of the additional parameters.

13. The processing apparatus of claim 12, wherein the memory stores a program and a data table.

14. The processing apparatus of claim 13, wherein the data table stores data associated with the first sample lot, data associated with the second sample lot, or the composite parameter structure.

15. The processing apparatus of claim 12, wherein the client terminal is a desktop computer, laptop computer, personal digital assistant, wireless handheld device, or mobile phone.

* * * * *